United States Patent
Hanina et al.

(10) Patent No.: US 11,200,965 B2
(45) Date of Patent: Dec. 14, 2021

(54) APPARATUS AND METHOD FOR RECOGNITION OF MEDICATION ADMINISTRATION INDICATOR

(71) Applicant: AIC Innovations Group, Inc., New York, NY (US)

(72) Inventors: Adam Hanina, New York, NY (US); Lei Guan, Jersey City, NJ (US); Dehua Lai, Elmhurst, NY (US)

(73) Assignee: AIC Innovations Group, Inc., New York, NY (US)

( * ) Notice: Subject to any disclaimer, the term of this patent is extended or adjusted under 35 U.S.C. 154(b) by 23 days.

(21) Appl. No.: 16/659,185

(22) Filed: Oct. 21, 2019

(65) Prior Publication Data

US 2020/0051244 A1    Feb. 13, 2020

Related U.S. Application Data

(63) Continuation of application No. 15/078,732, filed on Mar. 23, 2016, now Pat. No. 10,460,438, which is a
(Continued)

(51) Int. Cl.
*G16H 10/20* (2018.01)
*G06T 7/00* (2017.01)
(Continued)

(52) U.S. Cl.
CPC ........ *G16H 10/20* (2018.01); *A61M 5/31568* (2013.01); *G06K 9/6202* (2013.01);
(Continued)

(58) Field of Classification Search
CPC .... G06T 7/0012; A61M 5/31568; G06K 9/78; G06K 9/6202; G06F 19/34;
(Continued)

(56) References Cited

U.S. PATENT DOCUMENTS 3,814,845 A    6/1974    Hurlbrink et al.
5,065,447 A   11/1991    Barnsley et al.
(Continued)

OTHER PUBLICATIONS

Ammouri, et al., "Face and Hands Detection and Tracking Applied to the Monitoring of Medication Intake," Computer and Robot Vision, 2008. CRV '08. Canadian Conference on, vol. no., pp. 147, 154, May 28-30, 2008.
(Continued)

*Primary Examiner* — John W Miller
*Assistant Examiner* — Sean N. Haiem
(74) *Attorney, Agent, or Firm* — Fish & Richardson P.C.

(57) ABSTRACT

A method, system and computer program for confirming proper medication amount for a medication injection apparatus. The computer program causes a computer to perform the steps of providing one or more instructions on a display of a computing device instructing placement of an injectable medication apparatus including an indication of an amount of medication to be injected by the injectable medication apparatus, imaging by an image capture one or more images of the injectable medication apparatus including the indication of the amount of medication, and comparing by a processor of the computing device through recognition of the indication of the amount of medication, the indicated amount to a predetermined amount. One or more additional instructions may be provided on the display of the computing device to change the indication of the amount of medication if it is determined that the recognized indicated amount does not match the predetermined amount.

18 Claims, 13 Drawing Sheets

Related U.S. Application Data continuation of application No. 13/867,561, filed on Apr. 22, 2013, now Pat. No. 9,317,916.

(60) Provisional application No. 61/811,428, filed on Apr. 12, 2013.

(51) Int. Cl.

| | | |
|---|---|---|
| *A61M 5/315* | (2006.01) | |
| *G06K 9/62* | (2006.01) | |
| *G06K 9/78* | (2006.01) | |
| *G16H 20/10* | (2018.01) | |
| *G16H 20/17* | (2018.01) | |

(52) U.S. Cl.
CPC .............. *G06K 9/78* (2013.01); *G06T 7/0012* (2013.01); *G16H 20/10* (2018.01); *G16H 20/17* (2018.01)

(58) Field of Classification Search
CPC . G06F 19/3456; G06F 19/3468; G06Q 10/10; G06Q 50/22; G06Q 50/24
USPC .................. 705/3, 2; 348/143, 61; 604/189; 600/432, 420; 715/810
See application file for complete search history.

(56) References Cited

U.S. PATENT DOCUMENTS

| | | |
|---|---|---|
| 5,441,047 A | 8/1995 | David et al. |
| 5,544,649 A | 8/1996 | David et al. |
| 5,619,991 A | 4/1997 | Sloane |
| 5,646,912 A | 7/1997 | Cousin |
| 5,752,621 A | 5/1998 | Passamante |
| 5,764,296 A | 6/1998 | Shin |
| 5,810,747 A | 9/1998 | Brundy et al. |
| 5,911,132 A | 6/1999 | Sloane |
| 5,961,446 A | 10/1999 | Beller et al. |
| 6,151,521 A | 11/2000 | Guo et al. |
| 6,233,428 B1 | 5/2001 | Fryer |
| 6,283,761 B1 | 9/2001 | Joao |
| 6,380,858 B1 | 4/2002 | Yarin et al. |
| 6,409,661 B1 | 6/2002 | Murphy |
| 6,421,650 B1 | 7/2002 | Goetz et al. |
| 6,483,993 B1 | 11/2002 | Misumi et al. |
| 6,484,144 B2 | 11/2002 | Martin et al. |
| 6,535,637 B1 | 3/2003 | Wootton et al. |
| 6,611,206 B2 | 8/2003 | Eshelman et al. |
| 6,705,991 B2 | 3/2004 | Bardy |
| 6,879,970 B2 | 4/2005 | Shiffman et al. |
| 6,988,075 B1 | 1/2006 | Hacker |
| 7,184,047 B1 | 2/2007 | Crampton |
| 7,184,075 B2 | 2/2007 | Reiffel |
| 7,256,708 B2 | 8/2007 | Rosenfeld et al. |
| 7,277,752 B2 | 10/2007 | Matos |
| 7,304,228 B2 | 12/2007 | Bryden et al. |
| 7,307,543 B2 * | 12/2007 | Rosenfeld .............. G16H 50/20 340/870.01 |
| 7,317,967 B2 | 1/2008 | DiGianfilippo et al. |
| 7,340,077 B2 | 3/2008 | Gokturk |
| 7,395,214 B2 * | 7/2008 | Shillingburg ....... G06F 19/3462 705/2 |
| 7,415,447 B2 | 8/2008 | Shiffman et al. |
| 7,448,544 B1 | 11/2008 | Louie et al. |
| 7,562,121 B2 | 7/2009 | Berisford et al. |
| 7,627,142 B2 | 12/2009 | Kurzweil et al. |
| 7,657,443 B2 | 2/2010 | Crass et al. |
| 7,692,625 B2 | 4/2010 | Morrison et al. |
| 7,747,454 B2 | 6/2010 | Bartfeld et al. |
| 7,761,311 B2 | 7/2010 | Clements et al. |
| 7,769,465 B2 | 8/2010 | Matos |
| 7,774,075 B2 | 8/2010 | Lin et al. |
| 7,874,984 B2 | 1/2011 | Elsayed et al. |
| 7,881,537 B2 | 2/2011 | Ma et al. |
| 7,908,155 B2 | 3/2011 | Fuerst et al. |
| 7,912,733 B2 | 3/2011 | Clements et al. |
| 7,956,727 B2 | 6/2011 | Loncar |
| 7,983,933 B2 | 7/2011 | Karkanias et al. |
| 8,321,284 B2 | 11/2012 | Clements et al. |
| 9,514,131 B1 * | 12/2016 | Bochenko ........... G06F 19/3456 |
| 2001/0049673 A1 | 12/2001 | Dulong et al. |
| 2001/0056358 A1 * | 12/2001 | Dulong ............... G06F 19/3456 705/2 |
| 2002/0026330 A1 * | 2/2002 | Klein ..................... G06Q 10/10 705/3 |
| 2002/0093429 A1 | 7/2002 | Matsushita et al. |
| 2002/0143563 A1 | 10/2002 | Hufford et al. |
| 2003/0164172 A1 | 9/2003 | Chumas et al. |
| 2003/0190076 A1 | 10/2003 | Delean |
| 2003/0225325 A1 | 12/2003 | Kagermeier et al. |
| 2004/0100572 A1 | 5/2004 | Kim |
| 2004/0107116 A1 | 6/2004 | Brown |
| 2004/0155780 A1 | 8/2004 | Rapchak |
| 2005/0144150 A1 | 6/2005 | Ramamurthy et al. |
| 2005/0149361 A1 | 7/2005 | Saus et al. |
| 2005/0180610 A1 | 8/2005 | Kato et al. |
| 2005/0182664 A1 | 8/2005 | Abraham-Fuchs et al. |
| 2005/0234381 A1 | 10/2005 | Niemetz et al. |
| 2005/0267356 A1 | 12/2005 | Ramasubramanian et al. |
| 2006/0066584 A1 | 3/2006 | Barkan |
| 2006/0218011 A1 | 9/2006 | Walker et al. |
| 2006/0238549 A1 | 10/2006 | Marks |
| 2007/0008112 A1 | 1/2007 | Covannon et al. |
| 2007/0008113 A1 | 1/2007 | Spoonhower et al. |
| 2007/0030363 A1 | 2/2007 | Cheatle et al. |
| 2007/0078333 A1 * | 4/2007 | Abe .................... G01R 33/5601 600/420 |
| 2007/0118389 A1 | 5/2007 | Shipon |
| 2007/0194034 A1 | 8/2007 | Vasiadis |
| 2007/0233035 A1 | 10/2007 | Wehba et al. |
| 2007/0233049 A1 | 10/2007 | Wehba et al. |
| 2007/0233050 A1 | 10/2007 | Wehba et al. |
| 2007/0233281 A1 | 10/2007 | Wehba et al. |
| 2007/0233520 A1 | 10/2007 | Wehba et al. |
| 2007/0233521 A1 | 10/2007 | Wehba et al. |
| 2007/0273504 A1 | 11/2007 | Tran |
| 2008/0000979 A1 | 1/2008 | Poisner |
| 2008/0059228 A1 * | 3/2008 | Bossi .................. G06F 19/3418 705/2 |
| 2008/0077001 A1 * | 3/2008 | Ruscio .................. G16H 30/20 600/407 |
| 2008/0093447 A1 | 4/2008 | Johnson et al. |
| 2008/0114226 A1 | 5/2008 | Music et al. |
| 2008/0114490 A1 | 5/2008 | Jean-Pierre |
| 2008/0138604 A1 | 6/2008 | Kenney et al. |
| 2008/0140444 A1 | 6/2008 | Karkanias et al. |
| 2008/0162192 A1 | 7/2008 | Vonk et al. |
| 2008/0178126 A1 | 7/2008 | Beeck et al. |
| 2008/0201174 A1 | 8/2008 | Ramasubramanian et al. |
| 2008/0219493 A1 | 9/2008 | Tadmor |
| 2008/0275738 A1 | 11/2008 | Shillingburg |
| 2008/0290168 A1 | 11/2008 | Sullivan et al. |
| 2008/0297589 A1 | 12/2008 | Kurtz et al. |
| 2008/0303638 A1 | 12/2008 | Nguyen et al. |
| 2009/0012818 A1 | 1/2009 | Rodgers |
| 2009/0018867 A1 | 1/2009 | Reiner |
| 2009/0043610 A1 | 2/2009 | Nadas et al. |
| 2009/0048871 A1 * | 2/2009 | Skomra ............... G06F 19/3456 705/3 |
| 2009/0095837 A1 | 4/2009 | Lindgren |
| 2009/0128330 A1 | 5/2009 | Monroe |
| 2009/0159714 A1 | 6/2009 | Coyne, III et al. |
| 2009/0217194 A1 | 8/2009 | Martin et al. |
| 2009/0245655 A1 | 10/2009 | Matsuzaka |
| 2009/0318762 A1 * | 12/2009 | Segawa ................ A61B 1/041 600/118 |
| 2010/0042430 A1 | 2/2010 | Bartfeld |
| 2010/0050134 A1 | 2/2010 | Clarkson |
| 2010/0057646 A1 | 3/2010 | Martin et al. |
| 2010/0092093 A1 | 4/2010 | Akatsuka et al. |
| 2010/0136509 A1 | 6/2010 | Mejer et al. |
| 2010/0138154 A1 | 6/2010 | Kon |
| 2010/0255598 A1 | 10/2010 | Melker |
| 2010/0262436 A1 | 10/2010 | Chen et al. |

(56) References Cited

U.S. PATENT DOCUMENTS

| | | | |
|---|---|---|---|
| 2010/0316979 | A1 | 12/2010 | Von Bismarck |
| 2011/0021952 | A1 | 1/2011 | Vallone |
| 2011/0119073 | A1 | 5/2011 | Hanina et al. |
| 2011/0153360 | A1* | 6/2011 | Hanina ............... G06F 19/3456 705/3 |
| 2011/0161109 | A1 | 6/2011 | Pinsonneault et al. |
| 2011/0195520 | A1 | 8/2011 | Leider et al. |
| 2011/0275051 | A1 | 11/2011 | Hanina et al. |
| 2012/0009555 | A1* | 1/2012 | Hanina ................. G16H 40/63 434/262 |
| 2012/0075464 | A1 | 3/2012 | Derenne et al. |
| 2013/0041257 | A1* | 2/2013 | Nemoto ................ A61M 5/007 600/432 |
| 2013/0063579 | A1* | 3/2013 | Hanina ................. G09B 19/00 348/61 |
| 2013/0233627 | A1* | 9/2013 | Vidal .................... G01G 19/414 177/25.13 |
| 2014/0047384 | A1* | 2/2014 | Fewins .................. G16H 10/20 715/810 |
| 2014/0081659 | A1* | 3/2014 | Nawana ..................... G01L 5/00 705/3 |
| 2014/0081662 | A1* | 3/2014 | Bradrick .............. A61B 5/0022 705/3 |
| 2014/0316804 | A1* | 10/2014 | Tran ....................... G06Q 50/22 705/2 |
| 2015/0032059 | A1* | 1/2015 | Allerdings ........ A61M 5/31525 604/189 |

OTHER PUBLICATIONS

Batz, et al. "A computer Vision System for Monitoring Medication Intake," in Proc. IEEE 2nd Canadian Conf. on Computer and Robot Vision, Victoria, BC, Canada, 2005, pp. 362-369.

Bilodeau et al. Monitoring of Medication Intake Using a Camera System. Journal of Medical Systems 2011. [retrieved on Feb. 18, 2013] Retrieved from ProQuest Technology Collection.

Chen, Pauline W., "Texting as a Health Tool for Teenagers", The New York Times, Nov. 5, 2009, http://www.nytimes.com/2009/11/05/health/05chen.htmlr=1&emc.

Danya International, Inc., "Pilot Study Using Cell Phones for Mobile Direct Observation Treatment to Monitor Medication Compliance of TB Patients", Mar. 20, 2009, www.danva.com/MDOT.asp.

Final Office Action from PTO, Cited in AI-0001-U1 (U.S. Appl. No. 12/620,686), (dated May 8, 2012), 1-24.

Final Office Action from PTO, Cited in AI-0001-U2 (U.S. Appl. No. 13/558,377), (dated May 7, 2013, 1-29.

Final Office Action from PTO, Cited in AI-0002-U1 (U.S. Appl. No. 12/646,383), (dated May 8, 2012), 1-31.

Final Office Action from PTO, Cited in AI-0002-U2 (U.S. Appl. No. 13/588,380), (dated Mar. 1, 2013), 1-27.

Final Office Action from PTO, Cited in AI-0003-U1 (U.S. Appl. No. 12/646,603), (dated Feb. 1, 2012), 1-17.

Final Office Action from PTO, Cited in AI-0004-U1 (U.S. Appl. No. 12/728,721), (dated Apr. 12, 2012), 1-31.

Final Office Action from PTO, Cited in AI-0005-U1 (U.S. Appl. No. 12/815,037), (dated Sep. 13, 2012), 1-15.

Final Office Action from PTO, Cited in AI-0006-U1 (U.S. Appl. No. 12/899,510), (dated Aug. 28, 2013).

Final Office Action from PTO, Cited in AI-0008-U1 (U.S. Appl. No. 12/898,338), dated Nov. 9, 2012), 1-12.

Final Office Action from PTO, Cited in AI-0012-U1 (U.S. Appl. No. 13/189,518), (dated Jul. 23, 2013), 1-16.

Global Tuberculosis Control: A short update to the 2009 report, World Health Organization, (2009).

Huynh et al., "Real time detection, tracking and recognition of medication intake." World Academy of Science, Engineering and Technology 60 (2009), 280-287.

International Preliminary Report on Patentability, cited in AI-0001-PCT1 (PCT/US2010/056935) (dated May 31, 2012), 1-8.

Mintchell, "Exploring the Limits of Machine Vision", Automating World, Oct. 1, 2011.

Non-Final Office Action from PTO, Cited in AI-0001-U1 (U.S. Appl. No. 12/620,686), (dated Dec. 21, 2011),1-78.

Non-Final Office Action from PTO, Cited in AI-0001-U2 (U.S. Appl. No. 13/558,377), (dated Oct. 22, 2012), 1-21.

Non-Final Office Action from PTO, Cited in AI-0002-U1 (U.S. Appl. No. 12/646,383), (dated Dec. 22, 2011),1-78.

Non-Final Office Action from PTO, Cited in AI-0002-U2 (U.S. Appl. No. 13/558,380), (dated Oct. 4, 2012), 1-20.

Non-Final Office Action from PTO, Cited in AI-0003-U1 (U.S. Appl. No. 12/646,603), (dated Oct. 13, 2011), 1-74.

Non-Final Office Action from PTO, Cited in AI-0003-U1 (U.S. Appl. No. 12/646,603), (dated Jun. 13, 2013), 1-16.

Non-Final Office Action from PTO, Cited in AI-0004-U1 (U.S. Appl. No. 12/728,721), (dated Jan. 6, 2012), 1-31.

Non-Final Office Action from PTO, Cited in AI-0004-U1 (U.S. Appl. No. 12/728,721), (dated May 9, 2013), 1-25.

Non-Final Office Action from PTO, Cited in AI-0005-U1 (U.S. Appl. No. 12/815,037), (dated Mar. 28, 2012),1-17.

Non-Final Office Action from PTO, Cited in AI-0005-U1 (U.S. Appl. No. 12/815,037), (dated Jul. 18, 2013), 1-19.

Non-Final Office Action from PTO, Cited in AI-0006-U1 (U.S. Appl. No. 12/899,510), (dated Jan. 23, 2013), 1-20.

Non-Final Office Action from PTO, Cited in AI-0008-U1 (U.S. Appl. No. 12/898,338), (dated Jun. 19, 2012), 1-16.

Non-Final Office Action from PTO, Cited in AI-0012-U1 (U.S. Appl. No. 13/189,518), (dated Dec. 21, 2012), 1-10.

Non-Final Office Action from PTO, Cited in AI-0013-U1 (U.S. Appl. No. 13/235,387), (dated Sep. 12, 2013), 1-16.

Osterberg, et al., "Adherence to Medication", New England Journal of Medicine 2005; 353:487-97, Aug. 4, 2005.

PCT Search report and written opinion, Cited in AI-0001-PCT1 (PCT/US2010/56935, dated Jan. 12, 2011),1-9.

PCT Search report and written opinion, Cited in AI-0005-PCT1 (PCT/US2011/35093, dated Sep. 12, 2011),1-8.

PCT Search report and written opinion, Cited in AI-0006-PCT1 (PCT/US11/54666, dated Feb. 28, 2012), 1-13.

PCT Search report and written opinion, Cited in AI-0008-PCT1 (PCT/US11/54668, dated Feb. 28, 2012), 1-12.

PCT Search report and written opinion, Cited in AI-0012-PCT1 (PCT/US12/41785, dated Aug. 17, 2012), 1-10.

PCT Search report and written opinion, Cited in AI-0013-PCT1 (PCT/US12/42843, dated Aug. 31, 2012), 1-8.

PCT Search report and written opinion, Cited in AI-0018-PCT1 (PCT/US2012/051554, dated Oct. 19, 2012), 1-12.

PCT Search report and written opinion, Cited in AI-0019-PCT (PCT/US12/59139, dated Dec. 18, 2012), 1-15.

PCT Search report and written Opinion, Cited in AI-0020-PCT1 (PCT/US13/20026, dated Aug. 5, 2013), 1-14.

Super-Resolution, Wikipedia, (Oct. 5, 2010).

University of Texas, GuideView, Mar. 15, 2007, http://www.sahs.uth.tmc.edu/MSriram/GuideView/.

Valin, et al. "Video Surveillance of Medication intake", Int. Conf. of the IEEE Engineering in Medicine and Biology Society, New York City, USA, Aug. 2006.

Wang et al. "Recent Developments in human motion analysis." Pattern Recognition 36 (220) 585-601 (Nov. 2001).

Whitecup, Morris S., "2008 Patient Adherence Update: New Approaches for Success", www.guideline.com, The Trend Report Series, (Oct. 1, 2008).

\* cited by examiner

APPARATUS AND METHOD FOR RECOGNITION OF MEDICATION ADMINISTRATION INDICATOR

CROSS REFERENCE TO RELATED APPLICATIONS

This application claims the benefit of U.S. Provisional Patent Application Ser. No. 61/811,428 filed Apr. 12, 2013 to Hanina et al, titled Apparatus and Method for Recognition of Medication Administration Indicator, the contents thereof being incorporated herein by reference.

FIELD

This invention relates generally to patient compliance in medication administration protocol scenarios, and more particularly to an apparatus and method for the monitoring, through video capture, of one or more visible parameters included on a medication administration apparatus, employing these captured video parameters to confirm proper medication administration, and guiding such administration by a user. The invention preferably relates to the use of computer vision and activity recognition for determination of selection of proper titration level or other dose size indicator in accordance with an injectable medication administration apparatus.

BACKGROUND

Dr Lars Osterberg, M.D. and Dr, Terence Blaschke have reported in the New England Journal of Medicine, *Adherence to Medication*, (N Engl J Med 2005; 353:487-97) 2005 an alarming lack of adherence to required medication protocol, further noting that while the average rates of adherence in clinical trials is categorized as "high", this number still comprises only rates of 43 to 78 percent. Most importantly, the authors note "The ability of physicians to recognize nonadherence is poor, and interventions to improve adherence have had mixed results." *Adherence*, p. 487. The authors conclude "Poor adherence to medication regimens is common, contributing to substantial worsening of disease, death and increased healthcare costs." *Adherence*, p. 494. *The Trend Repot Series,* 2008 *Patient Adherence Update: New Approaches for Success*, October 2008, report similar discouraging statistics. This broad range may possibly contribute to the public confidence in the FDA approval process and the importance of continued surveillance of a drug throughout the process. Furthermore, it may help to explain why, according to the Journal of the American Medical Association (JAMA May 1, 2002), one out of every five new drugs that comes to market in the US is found to have serious or life-threatening adverse effects—unknown or undisclosed at the time of approval. It is against this backdrop of poor adherence, and potential danger to patients, that the present invention operates.

It has been widely recognized that methods and systems for insuring proper medication ingestion or administration by individuals are very important in defending against unnecessary sickness, deaths and other problems. Giving instructions and then letting patients fend for themselves has been shown not to work particularly well. This is because it is not only the improper ingestion of medicines that is the primary cause of medical danger. Rather, an overall lack of sufficient patient guidance is also part of the problem. As has been shown in regards to various public health medication administration situations, such as administration of tuberculosis medication by the WHO, Directly Observed Treatment (DOT) improves compliance of patients. *Global Tuberculosis Control: A Short Update to the* 2009 *Report*, World Health Organization, 2009. As is shown in this report, funding for implementing DOT programs is high. Thus, the ability to implement such a program with less of a financial burden would be desirable.

Traditionally, participants attend introductions and follow ups for clinical trials, or in other disease management situations, in-person. Once the initial start up has been performed, however, patients are typically on their own to confirm that they are properly taking their medication. Infrequent checkups, typically every few weeks or longer, have proven to be insufficient. A number of systems exist that provide instructions to a user regarding when to take a medication and records when the user indicates that a medication has been taken. U.S. Pat. No. 7,359,214 describes such a system. A device is provided that provides instruction to a patient regarding medications to take. Furthermore, the system may provide a method for determining that the prescription is appropriate given the patient's conditions, and other medications he or she may already be taking. The system may monitor the dispensing of medicine in accordance with a predetermined treatment protocol. While such a system provides many improvements for easing a burden on the patient, this system suffers in many ways and in particular in ways relevant to the administration of medication in an injectable format.

U.S. patent application Ser. No. 11/839,723, filed Aug. 16, 2007, titled Mobile Wireless Medication Management System provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence or ingestion of the medication, or the relationship of adherence to the efficacy or safety of the drug over time. When requiring adherence to a predetermined protocol for a clinical trial, this is particularly relevant. Similarly, there is no mention of non-pill based medications.

Therefore, it would be desirable to provide an apparatus that overcomes the drawbacks of the prior art.

SUMMARY

In U.S. patent application Ser. No. 12/620,686, filed Nov. 18, 2009, titled Method and Apparatus for Verification of Medication Administration Adherence, abandoned; U.S. patent application Ser. No. 13/558,377, filed Jul. 26, 2012, titled Method and Apparatus or Verification of Medication Administration Adherence, currently pending; U.S. patent application Ser. No. 12/646,383, filed Dec. 23, 2009, titled Method and Apparatus for Verification of Clinical Trial Adherence, abandoned; U.S. patent application Ser. No. 13/558,380, filed Jul. 26, 2012, titled Method and Apparatus for Verification of Clinical Trial Adherence, currently pending; U.S. patent application Ser. No. 12/646,603, filed Dec. 23, 2009, titled Method and Apparatus for Management of Clinical Trials, currently pending; U.S. patent application Ser. No. 12/728,721, filed Mar. 22, 2010, titled Apparatus and Method for Collection of Protocol Adherence Data, currently pending; U.S. patent application Ser. No. 12/815, 037, filed Jun. 14, 2010, titled Apparatus and Method for Recognition of Patient Activities when Obtaining Protocol Adherence Data, currently pending; U.S. patent application Ser. No. 13/189,518, filed Jul. 24, 2011, titled Method and Apparatus for Monitoring Medication Adherence, currently pending; U.S. patent application Ser. No. 13/235,387, filed Sep. 18, 2011, titled Apparatus and Method for Recognition of Patient Activities, currently pending; U.S. patent application Ser. No. 13/674,209, filed Nov. 12, 2012, titled Method and Apparatus for Identification, currently pending; and U.S. patent application Ser. No. 13/674,459, filed Nov. 12, 2012, titled Method and Apparatus for Recognition of Inhaler Actuation, currently pending; the contents of these applications being incorporated herein by reference, the inventors of the present invention have proposed a system, method and apparatus that allow for complete control and verification of adherence to a prescribed medication protocol or machine or apparatus use in a clinical trial or disease management setting, whether in a health care provider's care, or when self administered in a homecare situation by a patient.

These applications present the only medication management system that may determine whether a user is actually following a protocol, provide additional assistance to a user, starting with instructions, video instructions, and the like, and moving up to contact from a medication administrator if it is determined that the user would need or benefit from such assistance in any medical adherence situation, including clinical trial settings, home care settings, healthcare administration locations, such as nursing homes, clinics, hospitals and the like, and in clinical trial settings.

The inventive solution, in accordance with one or more embodiments of the invention, may provide a webcam software solution, for distribution by medical professionals or other interested parties to provide a training system for training patients to properly administer their injectable, or other non-pill or pill based medication, to automate direct observation of medication administration of injectable or other medications, and to provide an audit trail of medication adherence and patient behavior. The inventive system may visually and audibly track medication adherence of injectable and/or other medication during training and actual medication administration in clinical trials or other medication administration scenarios on webcam-enabled laptops, tablets, smartphones mobile devices and other platforms without real time human supervision. The inventive system may visually and audibly recognize a fixed series of actions, each comprising part of the medication administration process. The inventive system, method and computer program may also interact, visually or otherwise, to obtain medical or other information from one or more medical devices.

In a still further embodiment, one or more audio cues may also be employed. Thus, for example, in the case of an injectable medication, audio monitoring of sound from the injection apparatus may be performed and used to further confirm that the patient has in fact properly administered the medication. Therefore, not only may positioning of the injection apparatus in the correct location and relative angle be confirmed, but activation of one or more injection mechanisms by the patient may also be confirmed. Similar monitoring may also be performed for inhalable or other medications, such as listening for device actuation, patient inhalation or the like.

When applied to an injectable medication, the patient may be requested to confirm refrigeration or confirm proper sanitization of an injectable tip with an alcohol swab or the like, confirm that the needle is not bent, that an injectable solution or medication has not changed color, or otherwise become spoiled in a manner that is visually detectable. While online training and instructions may be available currently, the interactive nature providing feedback to the user regarding their use and following of protocol is critical in improving adherence and patient action.

In accordance with yet another embodiment of the invention, a selection parameter, such as an indicated titration level, dose size, or the like may be confirmed through the use of computer vision, character recognition or the like. Thus, instead of requiring a complex, expensive system incorporated into the injection apparatus, the simple visual display of one or more selection parameters may be employed, and recognized by the inventive system. In one preferred embodiment of the present invention, an injectable pen apparatus or the like may allow a user to dial in a level of medication to be applied in a single dose. This dialed in level of medication may be indicated with a display of a number, pair of numbers, or other indicator. A computer vision system employing a webcam, or other camera mounted on a mobile device, tablet or other portable computing device, or remotely placed from a processing apparatus, and transmitting data thereto, may be employed to recognize this selection parameter, and perform processing in response thereto.

The user may be encouraged to properly place or otherwise position the injectable pen apparatus through the provision of one or more instructions displayed to the user on a display, preferably a display of the mobile computing apparatus including the camera for imaging the injectable pen apparatus. The apparatus locally and in real time may confirm that the user is properly performing one or more steps to allow the system to read the one or more indicators on the injection apparatus. If the user does not properly perform the desired steps, and therefore the imaging apparatus is unable to read the one or more indicators, the user may be provided with an alternative instruction and/or guidance further instructing them to perform a particular step or set of steps to allow the imaging apparatus to determine the one or more indicators. Only after properly performing the desired set of steps, thus allowing for the system to read the one or more indicators, is the user able to move to the next step or next instruction. After reading the defined dialed in or otherwise selected medication level or other selection parameter, the mobile device or other computing apparatus may provide feedback to the user, instructions regarding use, changes in medication levels, side effects warnings, questionnaires, and the like to the user. This information may also be preferably stored and/or forwarded to a remote processing apparatus for analysis and display to a healthcare provider or other interested party.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION

Figure 1:
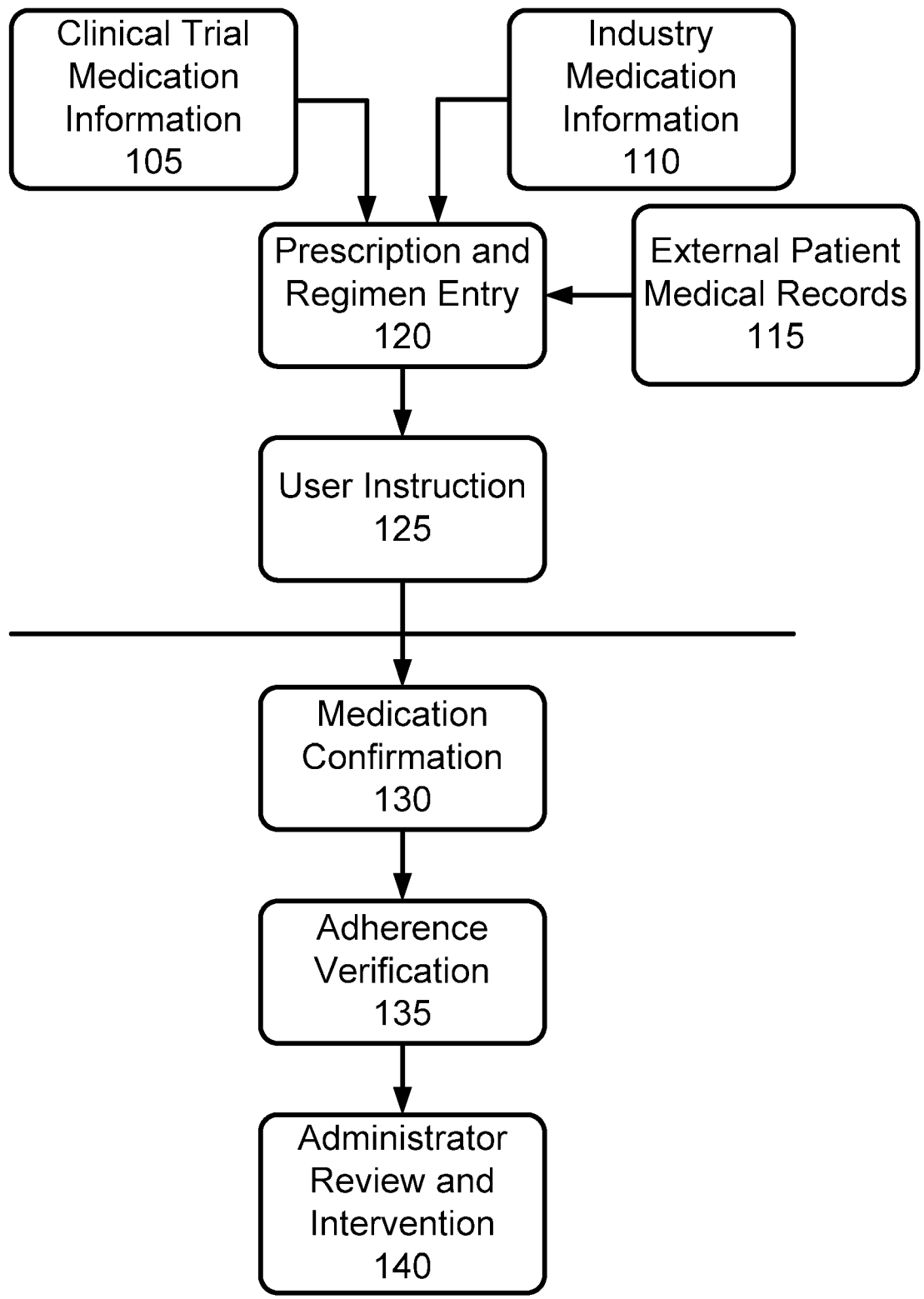
FIG. 1 is a flow chart diagram depicting a method in accordance with an embodiment of the invention.

The invention will now be described making reference to the following drawings in which like reference numbers denote like structure or steps. Referring to FIG. 1, a data flow overview in accordance with the operation of an embodiment of the present invention is shown. In accordance with this embodiment of the invention, information about a particular drug to be the subject of a clinical trial, to be employed in a public health or disease management situation, or the like, or other medication administration program or prescription may be provided in a database 105, and existing industry public or private medication information databases 110 are preferably employed to access prescription, interaction, application, and other available information about any number of proposed prescription and non-prescription medications and their possible interaction with the clinical trial or other medications. Further, patient medical records 115 may be used, and as will be described below, are preferably used in conjunction with the medication information and a medical professional's prescribing expertise to confirm that a patient is a good candidate for such a clinical trial, or medication administration program. These databases may be accessed in a manner known to one of ordinary skill in the art.

Once confirmed, a medication administration regimen in accordance with the clinical trial or other prescription requirements such as in a public health, medical practice environment or the like may be prescribed and entered into the system of the invention at 120. Once entered into the system, a particular prescription regimen may cause a set of user instructions, various training sequences and the like 125 to be generated and transmitted to an apparatus provided to a patient in accordance with an embodiment of the invention for access to the system of the invention. Such an apparatus may comprise a custom designed video and audio capture, analysis and transmission apparatus, a smart phone or other mobile device including a camera or other video and audio capture apparatuses, a netbook, laptop computer, desktop computer, tablet device or the like, local display and capture device with a remote processing system or the like, or other computing appliance allowing for the display of instructions to a patient, and allowing for the eventual capture, analysis and transmission of video, audio and other analysis information. When installing software on a user's own hardware system, it is preferred that the software detect and otherwise test or determine that the hardware attempting to be utilized by the patient is sufficient to implement the invention and is sufficient to run a software package provided in accordance with the invention. Thus, the software may check that a camera includes sufficient resolution, that a memory of the device is of sufficient size to allow for sufficient captured video storage, that audio may be properly captured, and that the transmission system includes sufficient bandwidth to transmit and receive captured video, audio, video instructions and the like. Step 125 may further be employed to allow for a standalone training sequence, as described.

In a clinical trial or other medication administration settings, patient instructions and various training sequences may be varied for different users to determine the best set of instructions, or may be varied based upon demographics, experience, or other factors that may require different types of instructions to be provided. It is further contemplated in accordance with an embodiment of the invention that multiple clinical trials or patient populations may be managed by a manager in accordance with the invention so that the invention contemplates a medication administration system that allows for a single point of management for all clinical trials or patient management groups associated with a particular manager or the like. The inventive system therefore allows for intervention by such a manager when medication is not taken, or is taken incorrectly, therefore encouraging patients to improve their behavior. A communications system may be incorporated into the inventive system to facilitate communication between the manager and one or more patients. Such management techniques in accordance with an embodiment of the invention may further be applied to various public health situations, disease management scenarios and the like.

Such user instructions and training sequences may include general instructions about the particular medication subject to the current trial or medication administration protocol, methods for administration, warnings about side effects, and concerns about drug interactions with common substances or medications, or other medications prescribed to the patient by the system or by another medical service provider. It is contemplated in accordance with an embodiment of the invention that such set of user instructions may be interactive, allowing a user to view additional information about such instructions or prescriptions as desired. These instructions may comprise written, audio or video instructions provided to the user on a display of the user apparatus. It is further contemplated that such instructions may indicate one or more movement sequences to be associated with a corresponding one or more medication administration sequences. A more in-depth description of the information provided at step 125 is depicted in FIG. 2.

Figure 2:
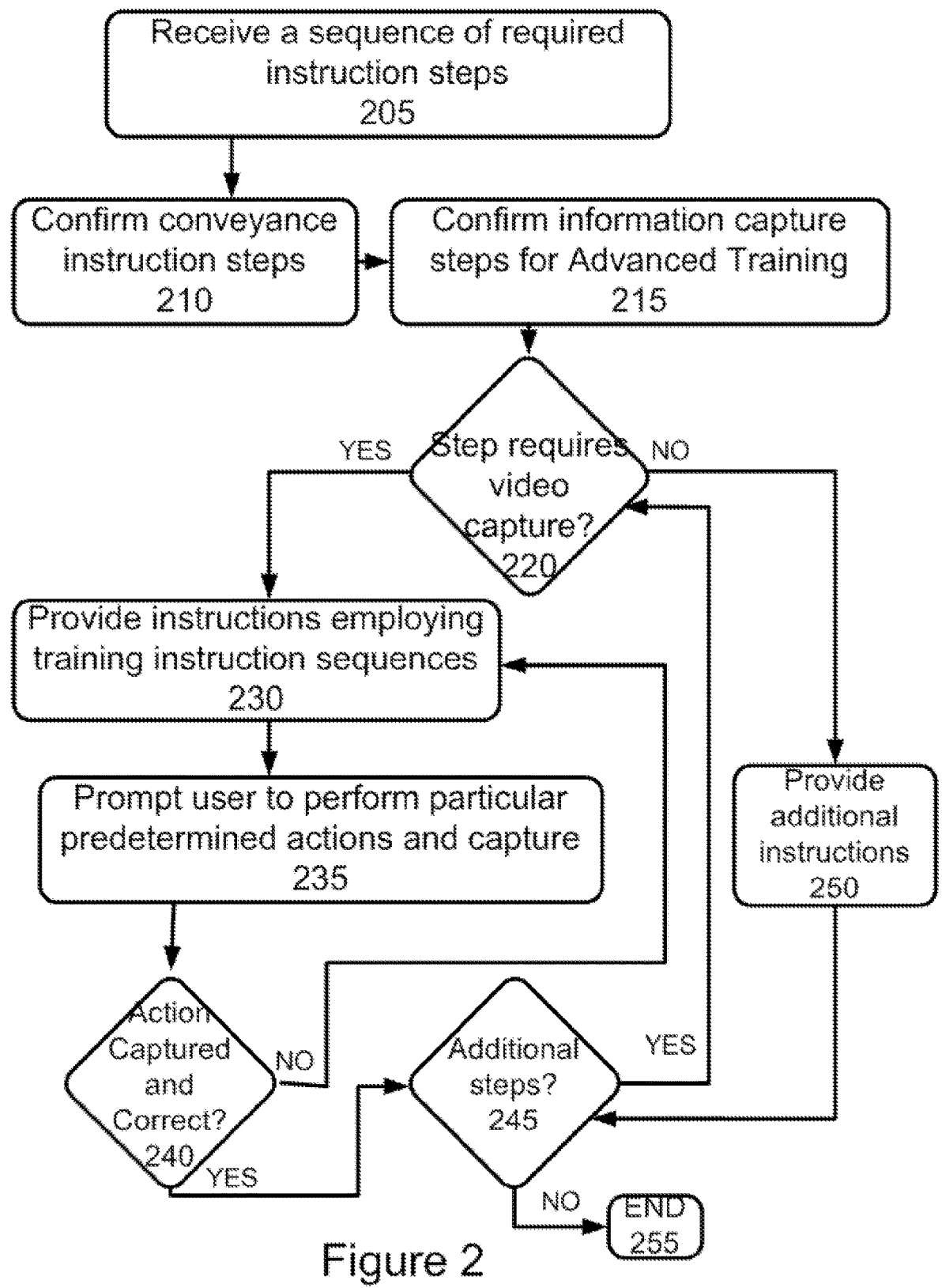
FIG. 2 is a flowchart diagram depicting a video sequence generation method in accordance with an embodiment of the invention.

As is shown in FIG. 2, the generation and provision of user instructions as set forth in step 125 first comprises the step of receiving a sequence of desired instruction steps at step 205. This sequence may be determined as described above in step 120. The system then may confirm whether one or more of the instructions steps require the conveyance of information to a patient at step 210. These conveyance steps may comprise a more conventional instruction step, such as the display of written information, comprise a more advanced instruction step, such as the conveyance of audible information, video instructions or the like, or may comprise an interactive instruction step, such as an interactive instruction sequence displaying a desired sequence of information to a patient, and then monitoring and confirming whether the patent has properly administered the medication. Various feedback mechanisms, such as alternative instruction and the like may be provided to allow the patient to try multiple times to perform proper administration if they first fail at properly performing the desired actions. Only after proper performance of a desired step or set of steps may the apparatus or system allow the user to progress to the next step. The apparatus may also provide varying encouragement or instructions to confirm that administration training has been performed properly. Thus, such an instruction and training sequence may include the eventual capture of video, audio and other information from the user. Therefore, at step 215, it may be determined whether one or more of the instruction steps will require the capture of information from the user, thus comprising an advanced interactive training sequence. Thereafter, each of the training steps requiring capture of video information from a user is confirmed at step 220. If no further video capture is required, and therefore various training or other interactive sequences have been completed, processing for step 215 then passes to step 250 where one or more instructions may be provided to the user. Processing then passes to step 245 for processing as will be described below. If it is determined that the capture of video and/or audio information will be required at step 220 for the current training step, then processing passes to step 230, and various instructional video, audio and other sequences may be provided to the user in an instructional sequence format.

After being shown a particular instructional sequence, preferably applicable to a particular step of a medication administration protocol sequence, then processing passes to step 235 where the user may be prompted to perform a particular action or sequence of movements, such as display of a medication administration apparatus to the camera for analysis of the medication administration apparatus by the camera and local or remote computing device. The user may request to be re-shown these sequences so as to practice with the interactive system as many times as necessary, and may also include audio or other instructions, so that the user is provided with a training sequence, thereby reducing variability of future performance of that action. When preparing to perform these actions, an alert system may be employed to warn the patient of any issues that may interfere with the proper capture of video and/or audio information, as may take place similarly when actually administering the medication. Thus, the user may be encouraged to properly perform these sequences, and avoid any possible actions that may hinder the proper recording and analysis of user actions by the system, thus acting as an interactive training module.

Figure 4:
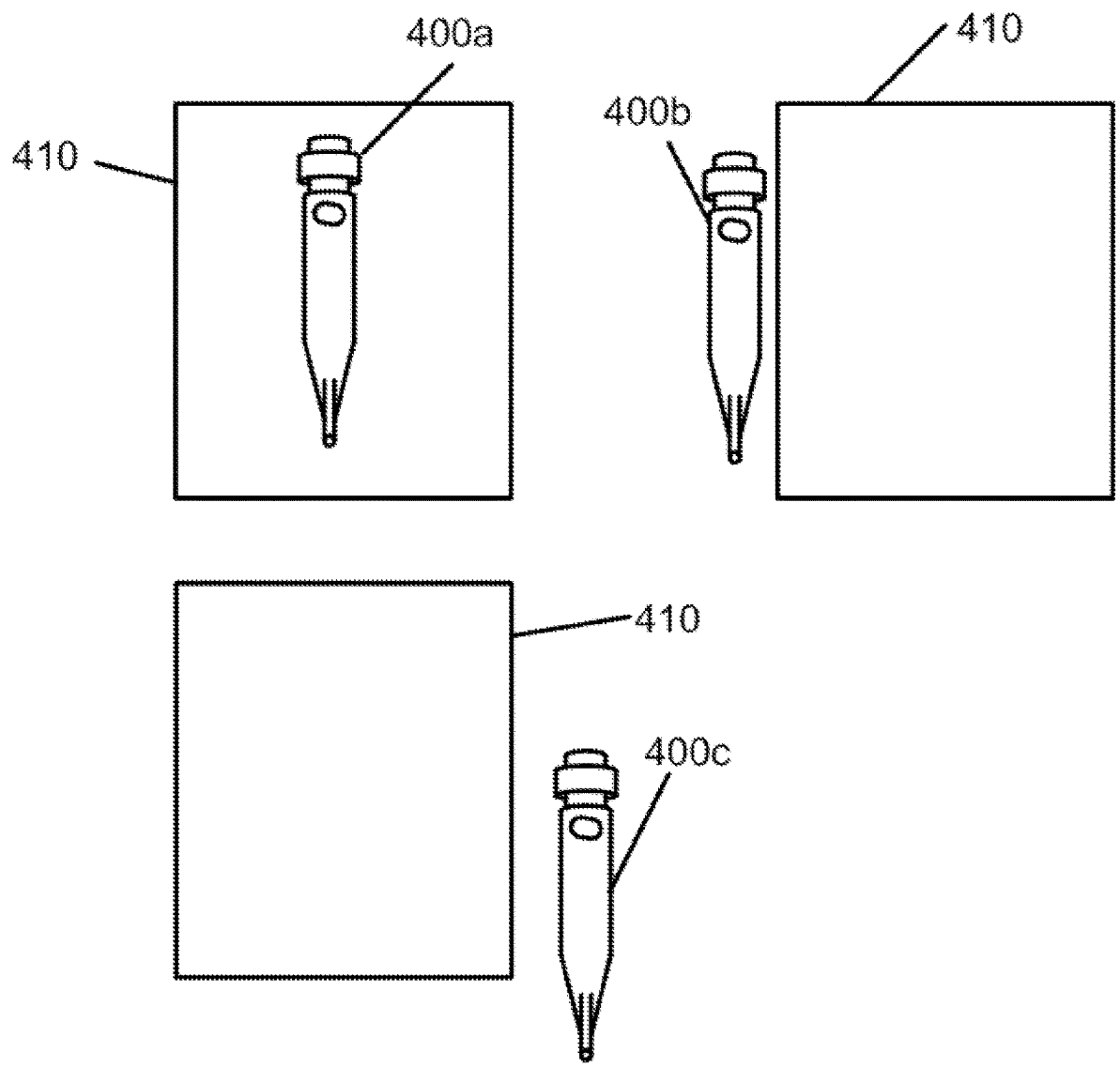
FIG. 4 is a depiction of a positioning process in accordance with an embodiment.

Thus, the user may be notified if they are sitting in a manner in which their actions cannot be properly captured, if they are blocked from the camera, the light conditions are insufficient or other environmental conditions may make it difficult to properly image a scene, object or person, if an object, such as an injection apparatus they are holding is in an improper location, or the like. As is shown in FIG. 4, a box 410 or other visual indicator may be provided on a display viewable by a patient using the system. A representation of the apparatus being held may be shown in a position relative to an optimal filming position for the use of, for example, an injectable apparatus for medication administration. Thus, while representation 400a is properly positioned, representation 400b is positioned to the left of the box, and representation 400c is positioned down and to the right of the box. In an injectable medication scenario, as in accordance with one or more embodiments of the present invention, the position of a patient body part may be further monitored along with, and to determine relative positioning in accordance with the injectable medication. Thus, not only may proper positioning be determined, but use of the proper body part may also be confirmed. In practice, the box may be made a red or other warning color or other indicator until proper alignment is achieved (including if a user or desired user body part is not positioned fully within a screen, the user is too close or far from the camera, or for any other reason), at which time the box may change to green or other appropriate color. Other indicators may also be employed. Further, audio clues may also be given to the patient, such as increasing frequency beeping as the optimal position is approached. Thus, in accordance with an embodiment of the present invention to be employed for injectable medications, the user is provided with immediate feedback on their position and the ability of their actions to be properly recorded and analyzed. As the user interacts with the system of this embodiment of the invention, such a scheme may be employed to provide continuous feedback to the user, and thus indicating whether the system is able to properly capture and/or analyze the actions of the user. If time is passed and the user is unable to properly position the apparatus, or to properly perform desired actions, additional guidance may be provided to the user in order to remedy such a situation, including but not limited to directional indications, voice commands, video images of proper technique, etc.

Figure 5:
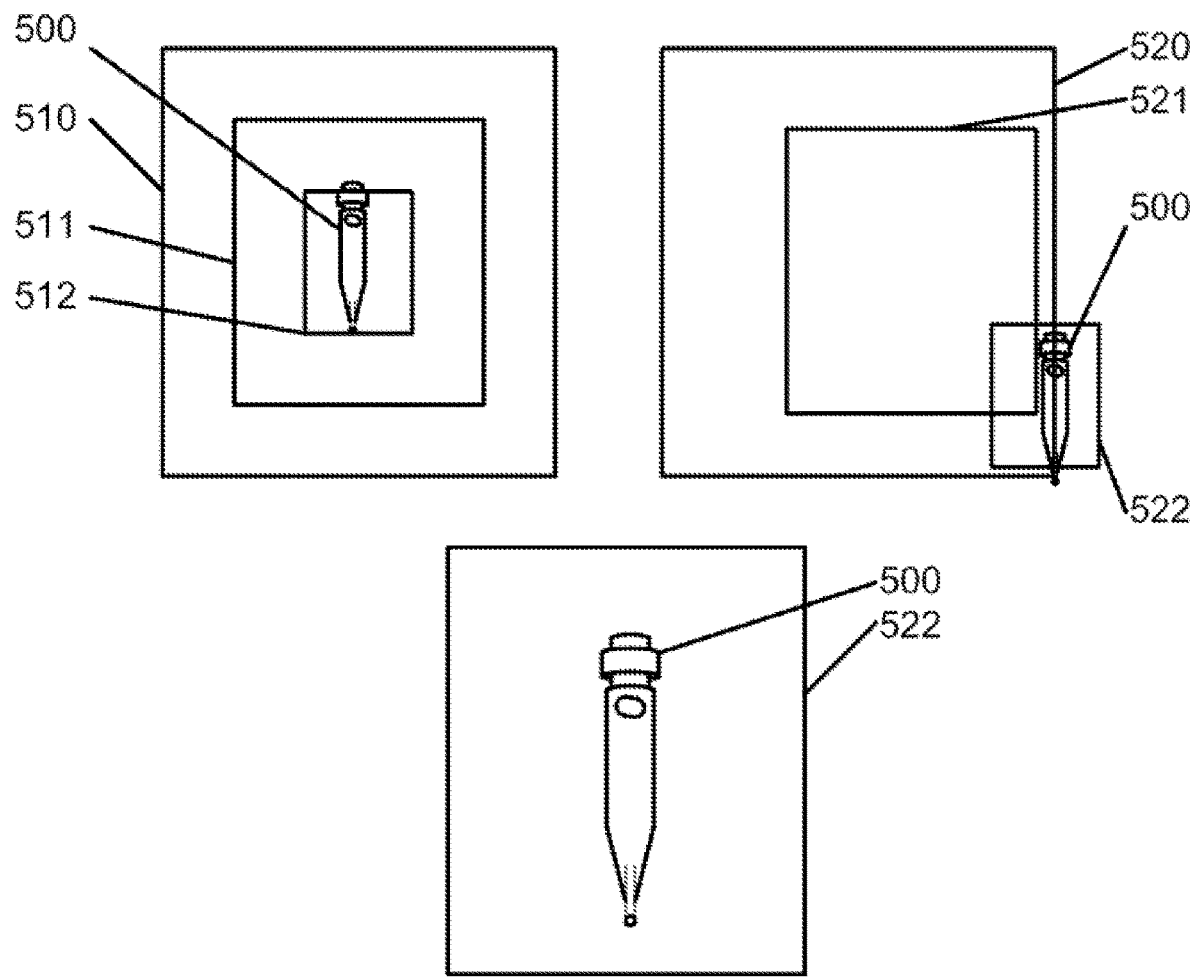
FIG. 5 is a depiction of another positioning process in accordance with an embodiment of the invention.

Thus, proper positioning of one or more objects, either absolutely or relative to another body part, may be determined, such as positioning an injectable medication delivery device relative to the body part of the user to receive the injection, or the like for imaging and processing in accordance with an embodiment of the invention. As is shown in FIG. 5, an injectable apparatus 500 may be indicated as properly positioned by a box 522, the box being green, for example, as in the description of FIG. 4. Such an object, however, is more likely to be improperly positioned not only left to right and up to down, but also in distance to the imaging apparatus, in accordance with one or more limitations of the imaging device, such as the resolution thereof, low light positions, and the like, and any affect such resolution might have on the ability of the imaging device to identify shape, color text or other coding, or the like associated with the object being imaged. Thus, if positioned too far away from the imaging apparatus, a sequence of boxes 510, 511, 512 and a small representation of inhaler 500 may be provided to alert the user to move the inhaler closer. If the injectable medication apparatus is not only too far away, but off center, boxes 520, 521, 522 may be provided to guide the user to move the injectable apparatus into proper position absolutely and relative to the relative body part of the user. Other indicators may also be employed. Functionality may be provided for positioning the injectable apparatus relative to a user body part to receive the injection, including relative angle and distance to the body part. By properly positioning such a device, the system may be employed to confirm the identity of such a medication, employing shape, color, labeling, and the like. In addition to determining identity of the medication, such processing may be used to determine safety of the apparatus, such as whether such an injectable device may have been damaged or tampered with. Further, the medication may be observed to determine any change in color or other characteristic of the medication that may suggest spoilage, improper medication, counterfeit medication or the like. The apparatus, in accordance with an embodiment of the invention, may thus ask the user to move the injectable device closer to or further away from the imaging apparatus, may change an ambient light sensitivity of the apparatus, or may otherwise change details of the image capture. As noted above, both color and audio prompting may be provided.

Figure 6:
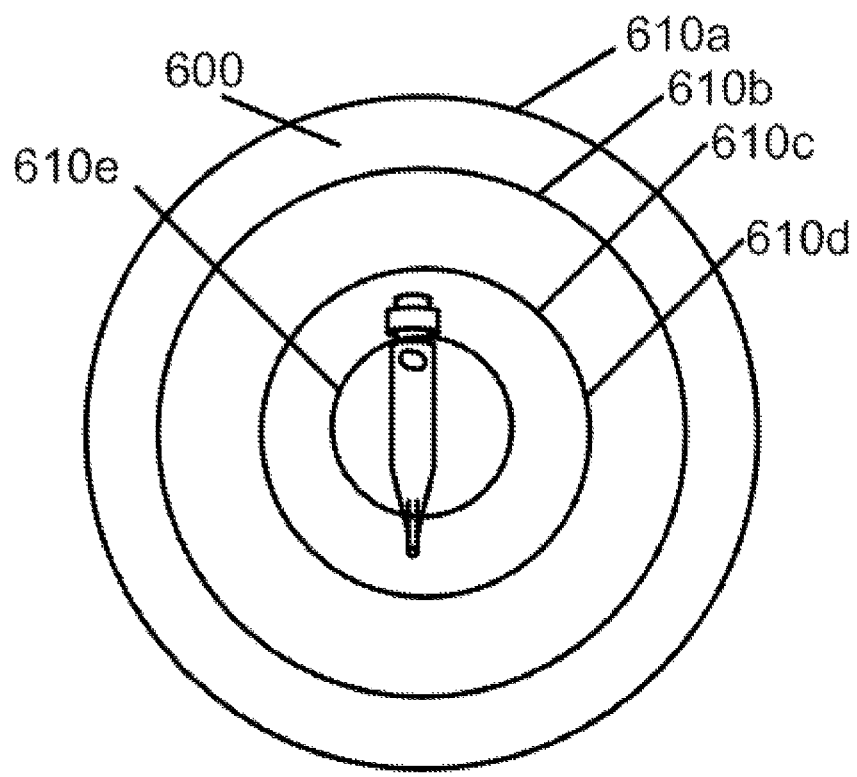
FIG. 6 is a depiction of yet another positioning process in accordance with an embodiment of the invention.

To the extent that positioning and orientation of the injectable (or other) medication administration apparatus or the like when being used is important, an alternative similar system may be employed. As is shown in FIG. 6, a set of concentric circles 610a-e may be provided to aid in the positioning of an injection apparatus 600. A center circle 610e may be provided with a solid center (not shown) upon proper placement of the medication injection apparatus. These circles may move as the boxes in FIG. 5, and may further use color and/or audio prompts to instruct the user. Further, as images of injection apparatus positions and orientations, or apparatus and hand positions and orientations, are to be captured and analyzed, the system may also preferably indicate not only proper positioning, but actual acquisition of a correct position and orientation sequence. In accordance with an additional embodiment of the invention, such recognizable positioning and orientation may further comprise a sequence of gestures and apparatus movement and orientation employed to ensure that the patient properly administers their medication. In accordance with an administration process, as noted above, the patient may first be trained to show a particular medication administration device or apparatus in their hand to the camera for imaging and recognition. The patient may then be asked to place the apparatus at an appropriate image acquisition position so that a selection parameter or other visible indicator on the apparatus may be observed. Thereafter, proper positioning of the injectable apparatus, through the process of monitoring movement and audible cues may be employed. Thus, through a predetermined sequence of actions that are captured, imaged and analyzed, evidence of proper administration can be recorded and analyzed.

Furthermore, during device setup, and in accordance with one or more embodiments of the invention, and as will be described below in greater detail, various additional aspects of medication and/or medication administration may be checked and confirmed. Thus, the system may employ such computer vision and activity recognition to determine a liquid color, liquid consistency or clarity, potential existence of particles, perhaps suggesting a spoiled medication, bubbles in the liquid, suggesting improper handling, in an injectable administration system. Through the use of the system, a number of administrations can be tracked, and a liquid or other level may be used to confirm the count, thus potentially allowing for the additional ordering of further medication, or other counting of injectable administrations without the need for expensive monitoring units. Also, dosage settings, if applicable on an injectable pen or other apparatus may also be confirmed before administration in a manner that will be described in greater detail below.

Figure 7:
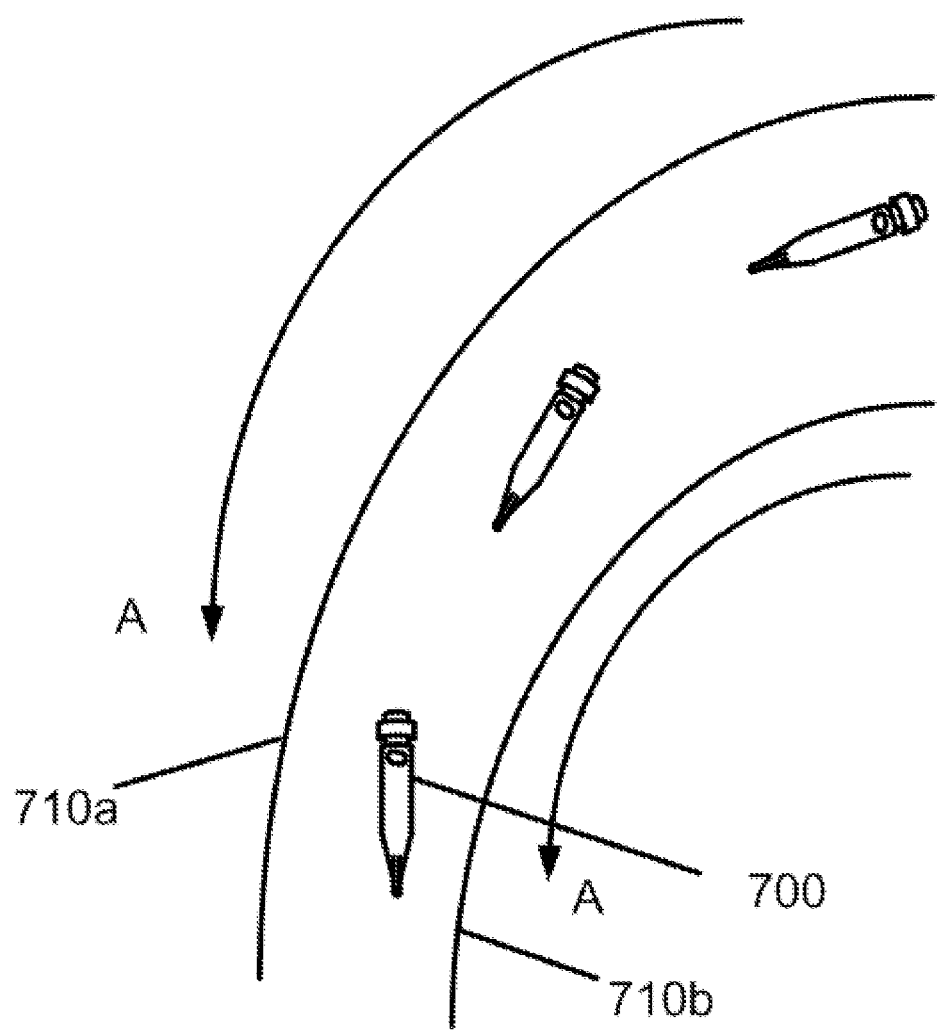
FIG. 7 is a depiction of a motion tracking process in accordance with an embodiment of the invention.

Furthermore, as is shown in FIG. 7, when tracking the movement of an injectable medication administration apparatus 700, it is preferable to depict to a patient whether they are holding the apparatus at a correct orientation, when the apparatus is in transit, or positioned at the administration sight. Thus, as is show in FIG. 7, an administration apparatus 700 is indicated to be reoriented from a horizontal to a vertical orientation through movement in the direction noted by arrows A. A set of guidance tracks 710a, 710b may be displayed to a patient and successive apparatus positions and orientations may be superimposed thereon. As the apparatus moves along the proscribed path, concentric circles such as those depicted in FIG. 6 may be employed to confirm proper location and orientation. Thus, in accordance with an embodiment of the invention, a virtual path may be shown to the user to ensure that the proper method of medication administration is followed. As noted above, color and/or audio sequences may also be employed. Thus, indication of, and guidance related to any desired movement of the apparatus may be provided the arc movement in FIG. 7 depicting an exemplary movement only. Therefore, in accordance with one or more of the positioning assistance schemes noted in FIGS. 4-7, a patient may be guided to properly present an object to an image capture device for capture and interpretation during the noted training phase, or (as will be described below) during a particular medication administration phase. Any of the display and notification techniques noted in any of these figures may be used in any of the other figures, in accordance with various embodiments of the invention. Further, these positioning techniques may be employed not only during initial training, but during any subsequent system process employing video image capture of people, objects, or any other entity to be imaged, or the use of audio information.

Referring back to FIG. 2, at step 240 these motions of the user may be captured and confirmed as being correct by one or more appropriate computer vision techniques, individual review by a human, or other appropriate determination process. If not correct, processing may return to step 230 to provide the instructions and example sequences again to the user, and may include one or more alternative instructions to aid the user to properly perform the desired steps of the medication administration sequence. Therefore, in accordance with one or more embodiments of the invention, repeated and/or additional instructions may be provided to the patient until training can be confirmed that the patient has performed the desired medication administration step sequence correctly, thereby aiding in limiting future variability in the actions taken by the patient during administration. Such instruction may take the form of analysis of a recorded user action, and comments on what the user may be doing wrong, and how this action may be improved. Once the user has received sufficient instruction, and it is therefore determined that the user has performed the action in a manner that is sufficiently similar to the instruction set, and substantially consistent over a number of performances of the action, processing then passes to step 245 where it is determined whether there are additional training steps to be presented, and therefore additional video sequences to be captured. Processing may only pass to step 245 after the desired or indicate process has been properly performed by the user or after a predetermined period of time has passed or a predetermined number of failures have occurred. The user may then be provided with further additional training to aid in proper performance of the one or more steps. If so, processing returns to step 220 for further processing. If not, processing ends at step 255.

Referring back to the lower portion of FIG. 1, the horizontal line indicates a time for patient administration of medication. At such time, the user may be notified to take their medication through any desirable communication and notification system, including text messaging, email, telephone call, automated calendar reminder or the like. While not explicitly shown, first, the identity of a user may be confirmed through the use of a facial recognition sequence, other biometric identification sequence, or other password identification system, or the like. Demographic information may also be requested or automatically collected for further identification and data analysis, and may be accumulated in accordance with one or more visual demographic information, such as age, skin color, eye color, or the like, doctor information, prescribing habits, pharmacy chain, cost point, etc. Such information may be employed to improve the system's ability to learn and predict patient behavior. Upon recognition of the individual, the system may display one or more data regarding the individual, such as, by way of example only, name, patient status, medication to be administered, calendar indicating to the patient when medication has been administered and if any administration times have been missed, and, selectively, a score indicative of a level of compliance of the individual with the medication protocol, if desired. Once identified and notified of a type of medication to be administered, the patient may display a medication administration apparatus, such as an injectable apparatus, or other medication form (including an inhaler, a pill bottle, a pill, or the like) to confirm that the medication is correct and is the currently prescribed medication to be taken through the use of text recognition, medication recognition, barcode or other code reading of one or more unique identifiers from the administration apparatus, pill bottle or the like, or other appropriate medication recognition scheme. In accordance with one or more embodiments of the present invention, as will be described below in greater detail, the user may be asked to show the medication administration apparatus to the camera to allow for the determination of the value of a particular selection parameter, such as a set titration level from a pen-type injector or the like.

The inventive system method and computer program may further act as an additional incentive program for the patient to properly take their medication, and may in turn give a patient other incentives, such as a running score, payment information, or other point systems if the patient is to be rewarded for properly taking medication. Thus, credit to buy information or other products or services from a website or store may be provided. For children, various animations may be provided, and pocket money or other credits may be provided to purchase items online or through one or more stores from supporting merchants may be provided. The display of such information may assist in convincing the patient to continue to properly take medication. This sequence of steps therefore acts as an audit trail each time a medication is taken, that can be reviewed later, to ensure that a patient is properly following a regimen. Any of the positioning schemes depicted in FIGS. 4-7 may be employed. Additionally, after confirmation or failure of confirmation of such administration, the user may be provided with a progress report regarding how they have performed over time, and further providing encouragement for future adherence. Additionally, notice of a next administration time may be provided, along with one or more messages from a healthcare provider regarding protocol changes, or other desired information.

Furthermore, use of a combination of visual and/or audio cues may be employed to further determine sequence and timing. Thus, not only should an injection apparatus be properly positioned, for example, but during use, an actuation by the patient should occur after proper positioning of the apparatus by the user. Thus, by visually and/or audibly confirming first positioning, and then actuation, this sequence of actions can be confirmed. Sound and visual signatures related to each of these actions may be employed to improve a confidence with which the system is able to confirm proper administration. Similarly, such an injectable apparatus may need to be properly positioned and maintained in a particular position after actuation, such as maintenance of a needle after actuation of the injection mechanism for a predetermined period of time. The various embodiments of the invention similarly may monitor such processing.

In accordance with the invention, confirmation of patient adherence to the prescribed administration schedule for the medication as prescribed by a healthcare provider, in a clinical trial, or in other prescription regimen including proper scheduled changes in, for example, titration levels, or other selection parameters may be determined. While such confirmation may take a number of forms, in accordance with the invention, a preferred method for such confirmation may include capturing a video and audio sequence of the patient actually displaying the injection apparatus or other apparatus including selection parameter, and then administering the medication. In a further preferred method in accordance with an embodiment of the invention, such a sequence for such confirmation may include employing a facial recognition sequence or other biometric confirmation that a particular patient is in fact receiving treatment, but may also provide for the ability to obscure the face or other identifying feature of a user, or otherwise encrypt such information to allow for the storage and use of such images while protecting the identity of the patient, a technique that may be beneficial when a medication administration manager is providing a general report about a clinical trial, and not trying to remedy a situation with a particular patient, or in particular in a public health or disease management scenario. Activity recognition, gesture recognition or other feature for determining whether a particular subject movement meets a predefined movement sequence may be employed to be sure that the patient is properly taking prescribed medication, i.e. the correct dosage.

Figure 3:
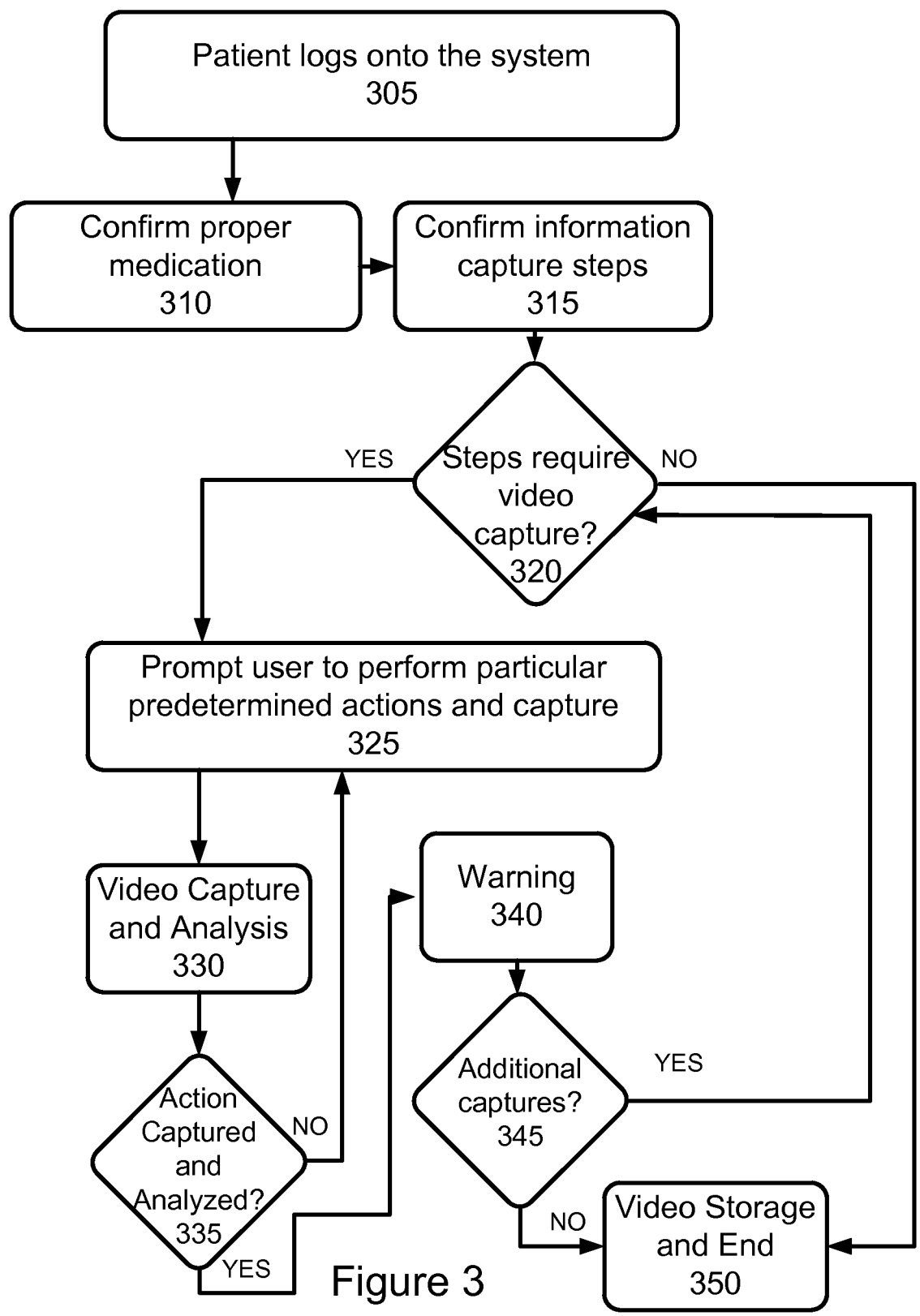
FIG. 3 is a flowchart diagram depicting a video sequence capture method in accordance with an embodiment of the invention.

Referring next to FIG. 3, a method in accordance with an additional embodiment of the present invention for performing audio and video capture and recognition of adherence to a prescribed protocol is described, as set forth in steps 130 and 135 of FIG. 1. In FIG. 3, a patient may first log into the system of the invention at step 305, employing the facial recognition, biometric recognition, password entry, or other patient identification method, and at step 310 proper medication is confirmed as noted above, through the user of bar code reading, text recognition, visual recognition employing video or still image recognition, or other medication recognition technique. In a particular embodiment of the invention, such visual recognition may be employed to read one or more selection parameters such as a dosing amount or titration level for a particular medication. Once determined, the user may be provided with advice on maintaining or changing the desired level or titration level of medication to be administered, may be asked to enter in further information to aid in determining an appropriate medication level, may be asked to couple, wirelessly or with a wire, one or more medical devices to further receive information therefrom. The patient may be reminded to log onto the system to take their medication through any type of reminder, such as a text message, email, phone call, automated alarm or the like. Next, at step 315 it may be confirmed that the process involved will include one or more information capture steps, and at step 320 it may be determined whether these information steps will include video capture. If not, video processing ends after storage of any non-video information.

(Alternatively, steps 315 and 320 may be excluded if it is determined that each confirmation sequence may employ video capture, then video processing may pass directly to step 325, as described below.) If it is confirmed at step 320 that one or more steps will include video and/or audio capture, processing then passes to step 325 where the user may be prompted to perform one or more predetermined actions, these actions being captured in a manner similar to the steps described above with respect to the embodiment of the invention noted in FIG. 2. These actions are preferably captured at step 330 and analyzed at step 335 to determine whether processing has been properly performed. As will be described in greater detail below, if proper action cannot be confirmed, processing returns to step 325, while if proper processing can be confirmed at step 335, processing may then pass to step 340 noting if any warnings are required, and then to step 345 to determine whether other video or audio/video captures are to be made, therefore confirming that additional processing steps have been properly performed.

Figure 8:
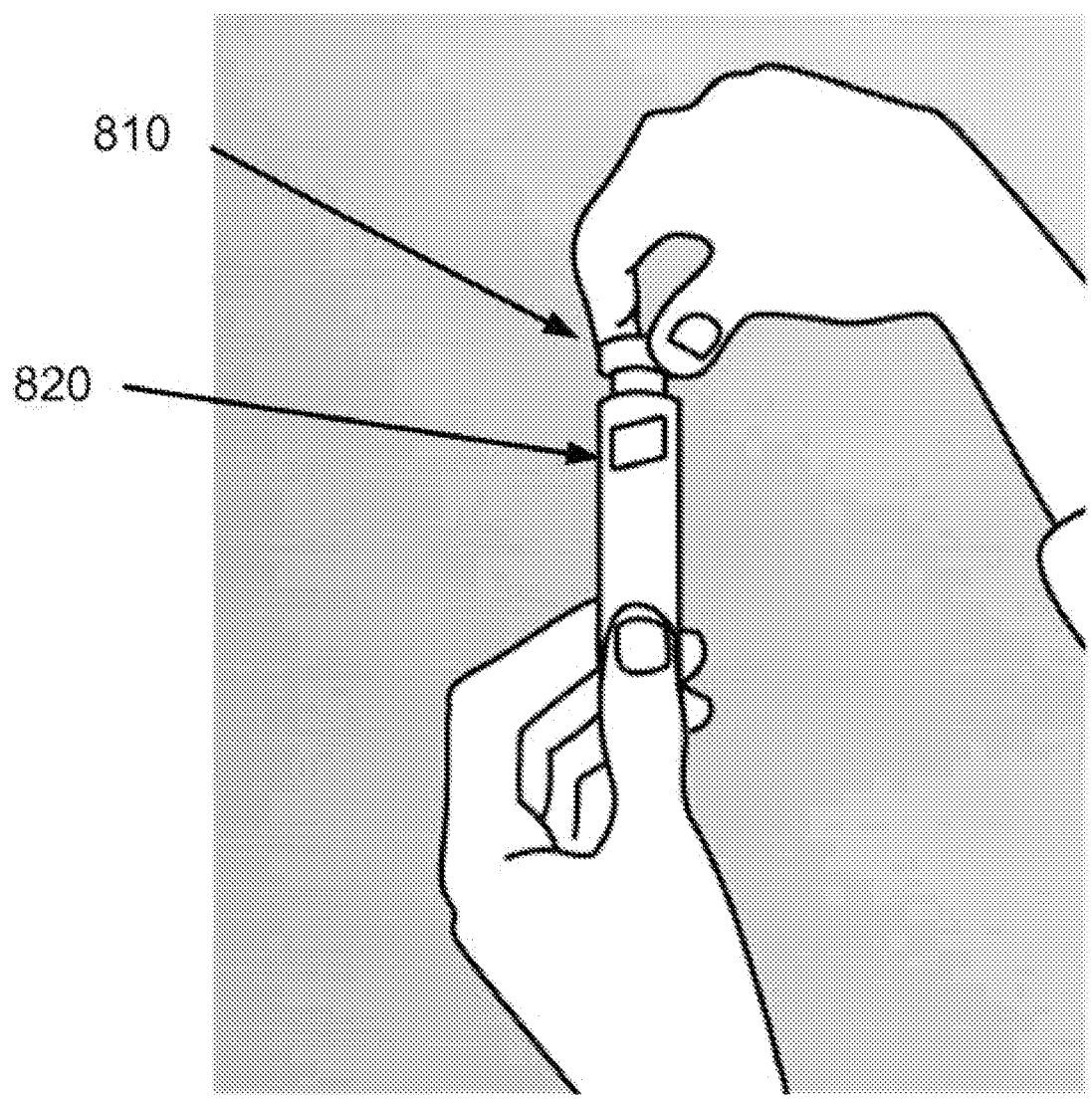
FIG. 8 depicts a user interacting with an injectable pen in accordance with an embodiment of the invention.

Positioning of the injectable medication apparatus or other medication may be performed in accordance with any of the techniques as described previously in reference to FIGS. 4-7 as part of step 325. In accordance with a still further embodiment of the invention, a particular set of capture steps to be employed with the reading of one or more specification parameters, such as with a titration level selected by a user and displayed on an injection pen apparatus, may be employed. As is shown in FIG. 8, a user is preferably first asked to set a titration level 820 of an injection type pen apparatus 810. This action is preferably performed by rotating a portion of the pen to change the titration level. Preferably, a number is displayed in a window of the pen to show a current selected level of titration. Of course, other methods for selection of such titration level, and other methods for display of such titration level or other selection parameter may also be employed.

Figure 9:
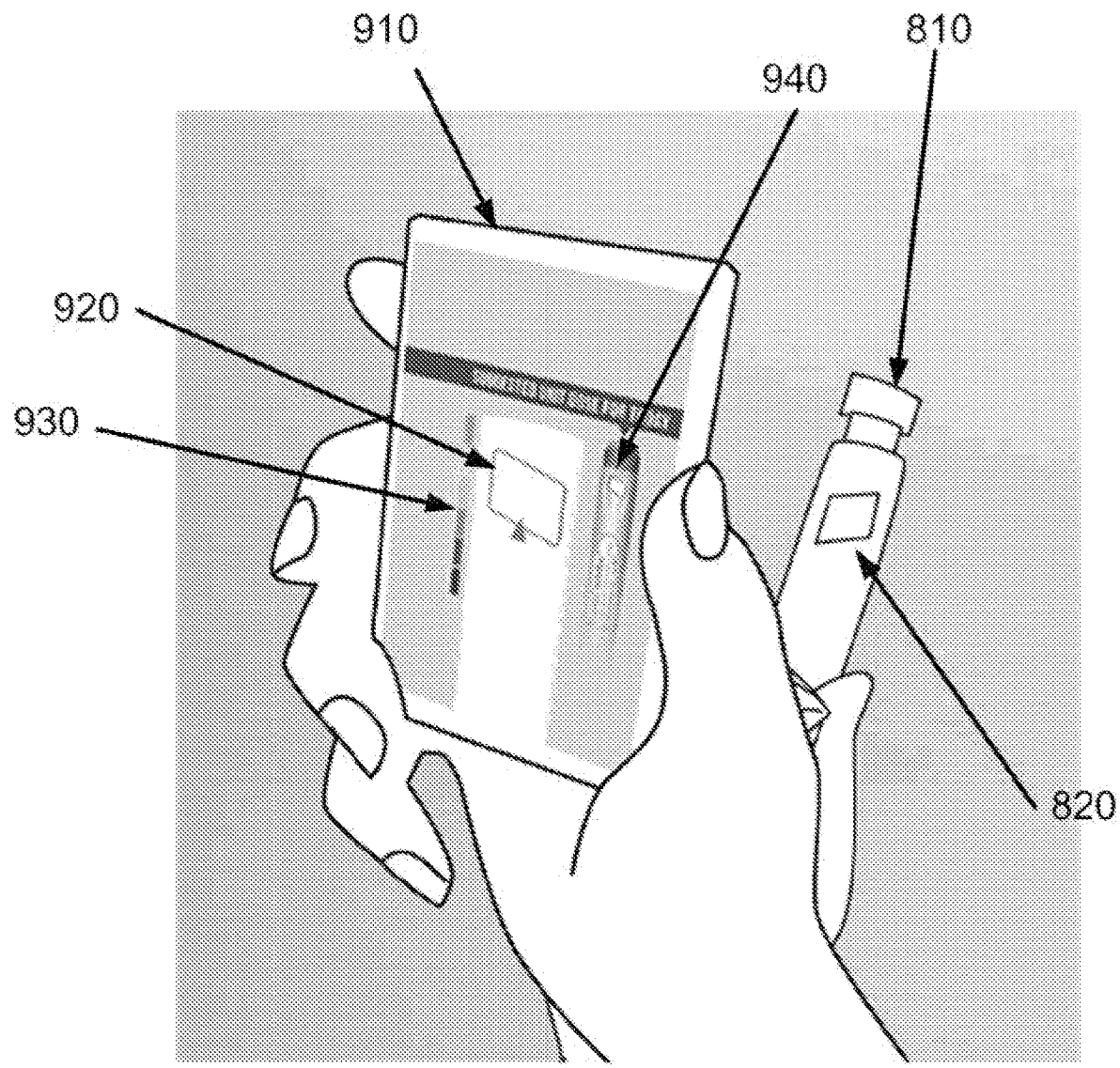
FIG. 9 depicts a user further interacting with the injectable pen in accordance with an embodiment of the invention.

Once the titration level is set by the user, as is further shown in FIG. 9, the user may be asked to take a set of video images of the injection pen, including imaging the titration level indicator, in a webcam of a portable computing device, such as a mobile phone, tablet, or any other computing device including a web camera. In FIG. 9, the user is shown as holding the injectable pen apparatus 810 behind a mobile computing device 910, and is this using the outward facing camera to image the apparatus, although the inward facing camera may also be used. Therefore, as is shown in FIG. 9, the mobile device 910 is preferably positioned to image the injection apparatus 810, including the titration level indicator 820. An image of the injection apparatus 810 and titration level indicator are preferable displayed on a display of mobile device 910. Included on the display of mobile device 910 are also one or more instructions 940 to encourage and help a user to properly use the system. A window 920 may be provided to encourage the user to match the image of the titration level 820 within the displayed window 920 to allow for proper reading thereof. One or more indicators 930 may also be provided to allow for an indication to the user of whether the injection apparatus 810 and associated titration level indicator 820 are properly positioned relative to displayed window 920. Various audio and/or visual instructions, prompts, encouragements or the like may be provided to the user to aid them in properly position the injection apparatus 810 relative to the mobile device 910.

Once properly positioned, mobile device 910 preferably reads the titration level indicator 820, and then may provide an indication of the determined titration level, and also may display one or more comments, instructions or the like to the user in accordance with the determined titration level. These comments may be related to one or more protocol suggestions for modifying a titration level or the like. Thus, based upon historical information, prescription information, personal information, demographic information, population information, one or more administration suggestions may be made, such as suggesting changing a particular titration level, or confirmation that the user is interested in maintaining a particular level for a particular amount of time.

Therefore, in accordance with one or more preferred embodiments of the invention, protocol information may be entered by a medical professional, service provider, user or the like. Information to personalize the particular instance of the application or the like may be entered into a mobile communication device with a camera, such as a smart phone, tablet computing device, computer or the like, upon which the computer program of the invention is to be run. Once setup, the user may be asked to enter further information including data related to one or more factors that may affect a desired titration level of medication. In a preferred embodiment, this may comprise one or more physical characteristics, such as height, weight, gender, age, etc.) or may comprise one or more measured parameters, such as blood sugar level, or the like. Based upon entry of such information, a desired titration level of a user may be suggested. This level may be suggested based upon processing locally of the computing device, or based upon processing or further information maintained at a remote location. Alternatively, the user may be asked to enter a titration level, thus allowing them to perform such calculations on their own. Various additional information may be provided form one or more coupled (wirelessly or wired) medical devices, such as a blood glucose monitor in the case of a diabetes indication. Other devices may also be employed as appropriate, and may include a bathroom scale to track weight changes, for example.

As noted above, when the time comes to monitor the use of the system and to aid and confirm proper injection of medication by the user, first the user is preferably shown one or more tutorial instructions in a manner noted with respect to FIG. 2, above. It is contemplated that these user instructions be interactive, and thus confirm that the user is properly performing each of the desired steps in response to the provided instructions before moving on to another set of instructions. Continued failures may result in the provision of one or more alternative instructions to further aid the user in properly performing each of the desired steps.

Figure 10:
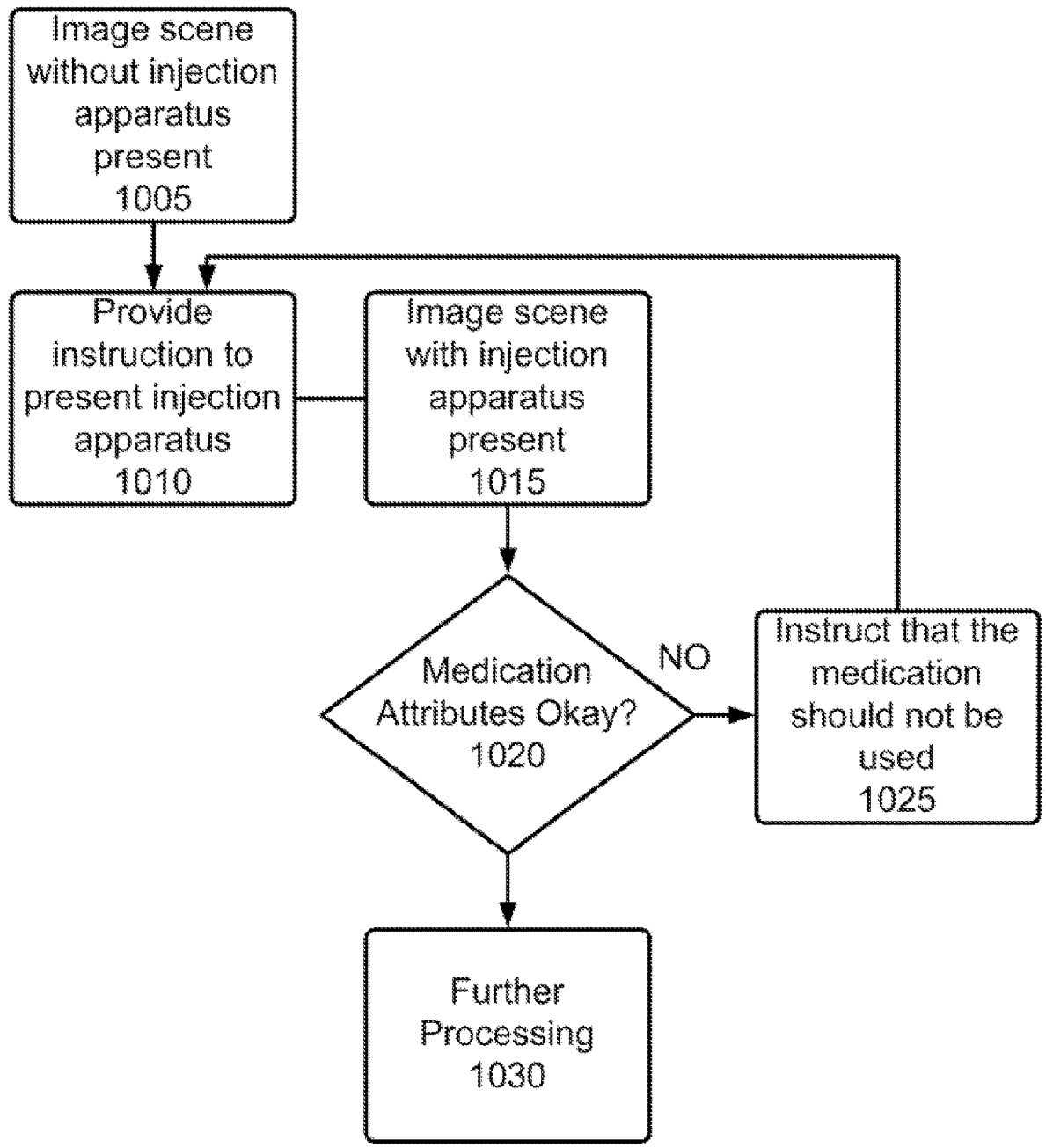
FIG. 10 is a flowchart diagram depicting an embodiment of the invention for confirming acceptable medication.

As noted above, and as further shown in FIG. 10, the processing steps may first ask the user to present the injection apparatus to the image capture device at step 1010 to determine, for example, that a color and observable consistency of the medication is proper. Thus, the system may confirm that the medication within the injection apparatus is a correct color and translucency or the like through the following process. The system may thus determine or otherwise take an image of a scene to learn the scene without the injection apparatus present at step 1005. The system may preferably segment the background based upon this image. Other segmentation schemes may also be employed. Once the background is learned, the user may be asked to present the injection apparatus to the capture device in accordance with one or more instructions at step 1010. One or more guide instructions, such as outlines displayed on a display, one or more arrows displayed on the display, one or more audio instructions (or any of the types of instructions noted above) or the like may be employed. The system may then visually detect the pen and a medication area within the pen, and may employ background subtraction to check whether the medication within the pen is clear, properly colored, or otherwise has one or more expected characteristics at step 1020. The system may also check to confirm that there are no unexpected particles within the medication. If the medication presents one or more undesirable or unexpected characteristics, the user may be warned not to use that particular medication or injection apparatus, and may be asked to change to another and perform these steps again at step 1025. This medication information may also be reported to a centralized location to determine faulty medication batches, inappropriate storage of medication, etc. Once the medication attributes are determined to be acceptable, processing passes to step 1030 so that next processing may take place.

Figure 11:
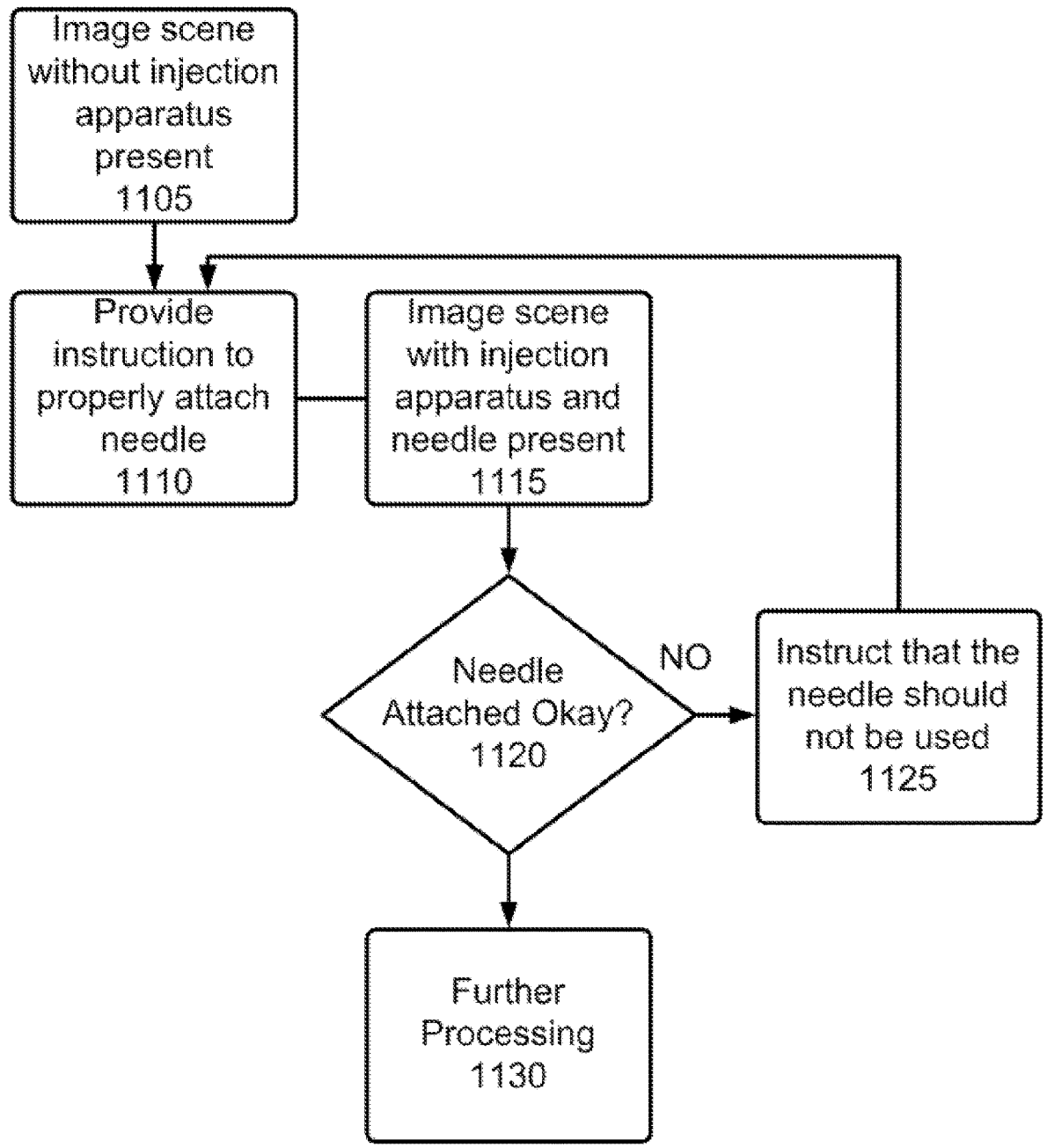
FIG. 11 is a flowchart diagram depicting an embodiment of the invention for confirming a safe needle of the medication injection apparatus.

If an injectable medication apparatus requires attachment of a needle (many do not as the needle may be incorporated into the apparatus in a retracted state, and is automatically extended and then retracted when administering medication), the system may confirm that a new needle with a cap or other appropriate packaging is presented to the image capture device. As is further shown in FIG. 11, first the scene is preferably imaged without the medication injection apparatus present at step 1105. (This step may be skipped, if unnecessary, or if the image may be employed from an earlier step. Similar displayed instructions may be employed to encourage and guide the user to properly attach the needle to the injection administration apparatus in step 1110. The system may therefore guide the user to attach the needle to the pen, and may detect the attaching needle to the pen action and confirm the completion of this step by checking the needle is attached to the pen at step 1115. The system may also confirm that the angle between the needle and pen is straight, and if not, guide the user to adjust the angle of the needle, or attach a new needle. At step 1120 the system may therefore determine whether the needle is properly attached. If not, then the user may be instructed to not use the needle at step 1125, or to reattach and adjust the needle, and processing may return to step 1110 to try another needle, or the adjusted needle. If it is determined that the needle is properly attached in step 1120, then processing may pass to step 1130 for further processing.

Figure 12:
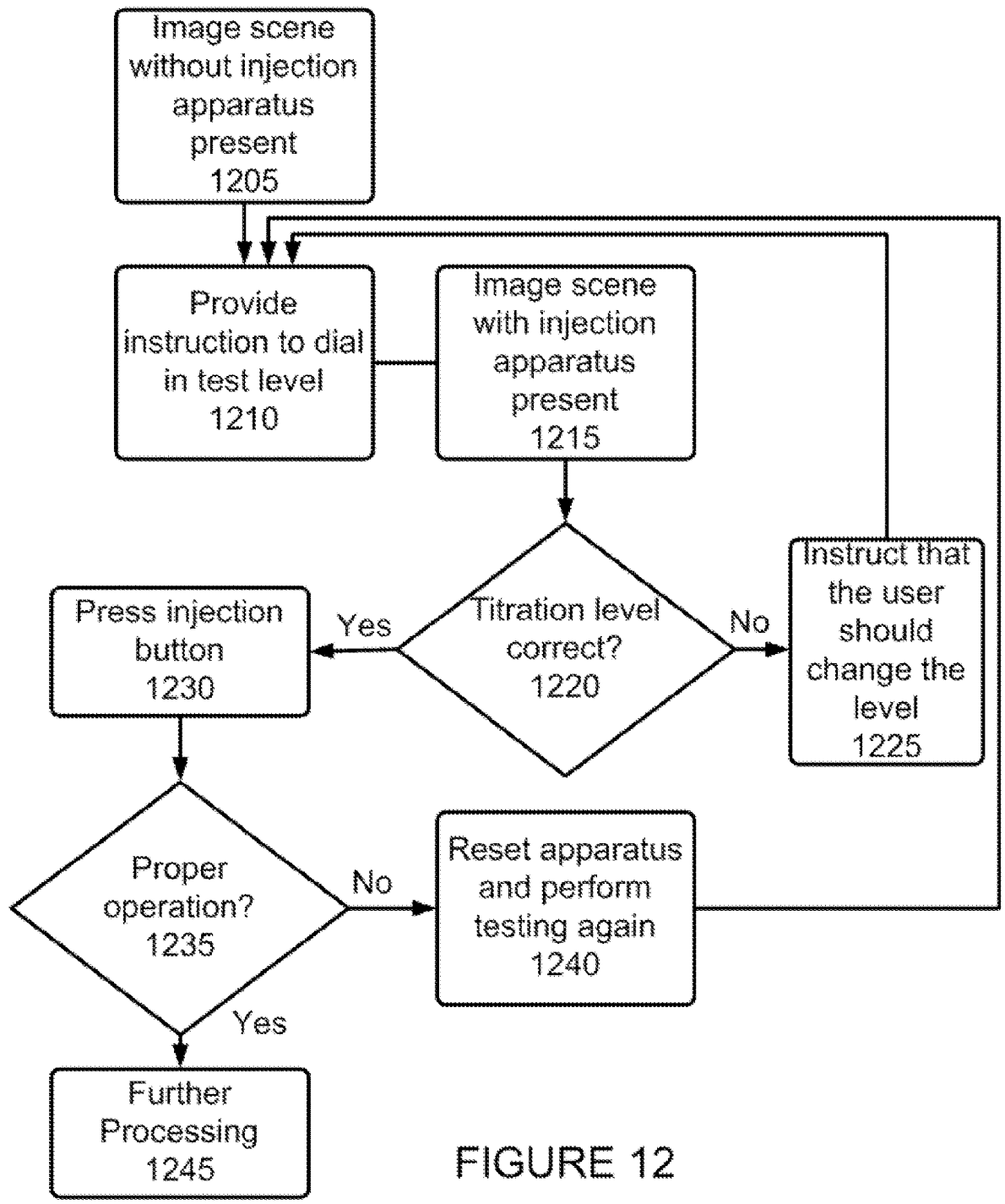
FIG. 12 is a flowchart diagram depicting a test sequence in accordance with an embodiment of the invention.

After setup, the user may be asked to perform a safety/system test of the apparatus. This safety test may be skipped if so desired. Thus as is first shown in FIG. 12, at step 1205, the scene may first be imaged without the medication injection apparatus present (or the scene may be used from one of the prior sequences, if the scene has not greatly changed). At step 1210, the user may then be guided to dial the dose to 2 units or some other predetermined test number for the titration level or other selection parameter. At step 1215 the scene is then preferably imaged with the injection apparatus present. This dial may be confirmed through one or more computer vision sequences in accordance with the invention at step 1220, and preferably in accordance with the process described above in accordance with FIGS. 8 and 9. Thus, the system may determine that the titration level has been set to "2", for example. Detailed steps for making this determination, and the remainder to the test sequence, may be performed in accordance with the processes described in reference to FIGS. 8 and 9, and may further include the following steps.

The step of testing whether the titration level is correct may further include the steps of guiding the user to hold the injection pen straight up, and detecting the injection pen. In order to confirm that the injection pen is pointing straight up, the angle between pen and horizontal line (bottom of the image) is measured and confirmed that it is approximately 180 degrees. Of course, detection of one or more other relative positions of the injectable medication apparatus, such as an injectable pen, may be employed. As noted above, one or more instruction prompts may preferably be employed to guide the user, and may include one or more of audio, video, text or other instructions. The positioning step may, as noted above, ask the user to position the injectable medication apparatus so that a titration level or the like may be read from the window thereof. Once read in a manner as described above, if it is determined that the test level is not set to the predetermined level, such as "2" for example, the user may be prompted at step 1225 to once again set the level to "2." The user may be provided such instructions for a predetermined number of times before being told to get a new injection apparatus, for example.

If the inquiry at step 1220 is answered in the positive, and it is therefore determined that the titration level for the test sequence has been properly set, processing may pass to step 1230 where the user is preferably guided to press injection button to actuate the system. Such actuation may be detected by the system, by one or more of audio and video detection, to determine proper operation of the apparatus at step 1235. Furthermore, in a situation where the titration or other medication level returns to zero after actuation, the system may determine that such a change has been made, also in step 1235, as part of the test procedure. Finally, if the injectable medication apparatus is completely imaged by the imaging device, the system may confirm actuation of the needle, such as movement thereof out of the injectable medication apparatus housing and/or if a fixed position needle, medication emanating therefrom. Decision fusion or other processing system may be performed in accordance with the three detection results to confirm success of the safety test.

If it is determined that the safety test sequence has failed at step 1235, processing may pass to step 1240 where the user may preferably be provided with notification thereof on the display of the mobile computing device, or other computing device, and may be asked to try to perform the safety test again. Alternative or other instructions may be provided in a case where the user is unable to follow the instructions for any reason. If after a predetermined number of tries the safety test cannot be properly performed, the system may preferably guide the user to change to another needle, if appropriate, and if the safety test still cannot be performed, then the user may be advised to switch to another injectable medication apparatus and perform the safety test with the new apparatus. Once the safety test has been properly performed, processing may then proceed to step 1245 for further processing to monitor the user administering the injectable medication.

Figure 13:
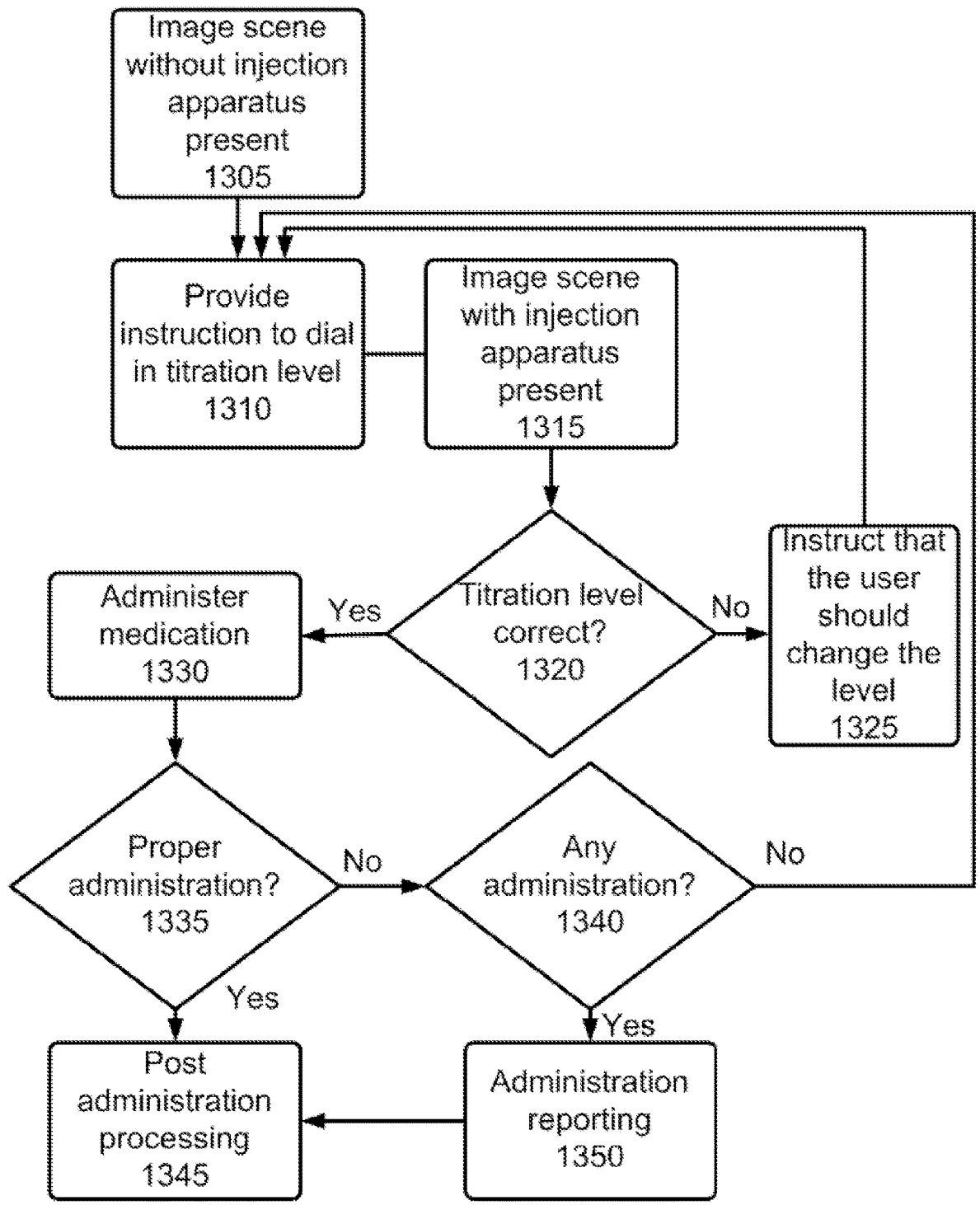
FIG. 13 is a flowchart diagram depicting processing in accordance with an embodiment of the invention.

Once the safety test has been performed, or of the safety test is not to be performed, the inventive method, computer program or system may then monitor administration of the injectable medication by the user, as will be further described in greater detail making reference to FIG. 13. As is shown in FIG. 13, first at step 1305, the scene is preferably images without an image apparatus present, or the empty scene may be employed from one of the earlier sequences (or may be skipped entirely). Then, processing preferably passes to step 1310 where the user is provided with one or more instructions for proper medication administration, including a reminder to the user of the correct dose based on protocol. Preferably, the user may receive a reminder on their mobile computing device, by email, text messaging, or by any other appropriate method that it is time to take their medication. Alternatively, the user may simply start the application/app/system and indicate a need or desire to take their medication, or an alarm may be provided for automatically starting the application when the timing is appropriate. This may be appropriate when medication is to be taken in reaction to a particular situation, rather than on a regular maintenance schedule. Once opened and started, the user may be reminded of the dose they are to administer (also in step 1310), or they may be asked to perform one or more tests to determine this dose, asked one or more questions to automatically determine the dose, asked to perform one or more sequences using a medical device coupled with, or designed to send information to, the apparatus or simply enter the desired dose. This dose may be different from the recommended dose for any number of reasons, including eating improper foods or amounts, eating or drinking at a wrong time, anticipation of an event coming on, etc. Upon recognition of one or more out of character medication administrations, the user may be asked one or more questions related to the change to determine one or more reasons for the change. A healthcare provider, pharmacist or the like may be alerted as appropriate based upon a determination of running out of medication, danger to the patient, side effects discouraging use, etc. The user may then be asked to adjust the injectable medication administration apparatus to the correct dose, by rotating a portion of the apparatus, as noted above, or through any other appropriate manner.

Processing then preferably passes to step 1315 where the scene is imaged including the apparatus set at the correct titration level, or including one or more other set selection parameters. In a manner similar to that noted above with respect to FIGS. 8 and 9, and the safety test noted above, the dialed in titration level may be determined in accordance with the computer vision character recognition on the injectable medication apparatus. Thus, as is noted above, the system preferably detects the apparatus, detects the area where one or more digits indicating the current titration level, and finally actually detects and reads this titration level. In one or more preferred embodiments of the invention, once this number is detected, it may be determined if this is a correct level in step 1320. If incorrect, the user may be notified of the error, and asked to change to the correct level at step 1325. The user may further be perhaps questioned as to whether they wish to change their titration level to the indicated level. This level may be determined based upon prior titration levels, or one or more planned changes in titration level from a last level in accordance with a protocol. Thus, the user may be asked to increase level a bit each day, or some predetermined amount after a predetermined number of days have passed, in accordance with one or more predetermined protocols. Thus, in such a case, the new medication level may be provided to the user in the instructions in step 1310, and if not properly implemented, reminders may be provided in step 1325

It should be noted that if the user needs to inject more medication than a particular medication injection apparatus can currently provide, the system may monitor the user, and allow them to indicate that a first apparatus will provide the first injection, and that a second apparatus will provide the second. Thus, the system may preferably remember the amount of the first injection level, and instruct the patient to use the second apparatus to administer the remainder of the injection. The user may be encouraged to provide this second injection within a predetermined period of time after the first injection. The safety test noted above may preferably be performed on any such new injection apparatus.

Once the injection apparatus has been properly set up, administration may be guided by the system at step 1330, and in particular as noted above, the system may detect that the injection apparatus is placed against a correct body part, at a correct angle, for example. The system may further check that the needle has been inserted into the body. These steps for positioning and insertion may be performed by determining that the angle between the pen and body surface is approximately 90 degrees, or through some other method.

After proper positioning has been determined, in the manner as noted above, the system preferably detects the action of pushing the injection button by the user, preferably in response to one or more instruction prompts provided to the user by the system, thus determining proper administration in step 1335. As noted above with respect to the safety test, the system may also confirm that the titration level indicator number returns to zero, or other indicator of a completed medication administration. Once the system detects the injection behavior has been properly performed, in order to ensure that the user maintains the apparatus in a proper location for a predetermined period of time, a time or other countdown or reminder may be displayed to the user on a display of the mobile or other computing device at step 1345. In order to automatically determine that the user has properly maintained the position of the injection apparatus, the system preferably monitors the angle between the injection apparatus and body surface area, confirming that the apparatus remains at a 90 degree angle for 10 seconds, for example. The system may also confirm that the actuation button is depressed during this time, if required by the apparatus.

Once the timing has passed, the user may then be guided by the system to remove the needle and apparatus from the body part receiving the injection. The system preferably guides the user to remove the needle and to put the needle cap on the needle. The system preferably confirms these steps detecting that a cap has been placed on top of the pen area, and that a needle is no longer visible to be detected. The system may then guide the user to screw on or otherwise secure the cap for safer storage and transport.

If it is determined that proper operation was not performed at step 1335, then the system further determines whether medication was provided at all. If no medication was provided, processing may return to step 1310 for reinstruction to the user on medication administration. If it is determined that medication has been administered, and therefore even though not completely proper, the system cannot ask the user to re-administer, processing may proceed to step 1350 to provide reporting related to the improper administration, and then to step 1345.

In addition to performing these guiding steps, the inventive system preferably performs one or more additional valuable features. First, the system may track how long a particular injection apparatus has been used, and/or how much medication has been administered from the particular injection apparatus. Reminders may be provided to the patient if the pen is expired or needs to be refilled as the medication has been used up, or has been nearly used up. Such a determination may be made based upon current medication levels and expected usage by the patient, along with anticipated refill lead times, if appropriate. The system may alternatively visually recognize a lot number, expiration date or the like in the apparatus to notify the user of an expired status. Furthermore, various usability data from one or more users may be employed and used for data mining. This can be helpful in figuring out a problematic medication (i.e. if an administration sequence is difficult for one or more users or patient populations), or whether more training is needed for one or more individual or groups.

The system may further provide a questionnaire in accordance with the administration confirmation, thus asking users about their general health, side effects or any other questions. These responses may then be employed to analyze the possible effects of medication, or the reason why a user may have failed to take medication at a particular time, or the like. In addition to such questions, other side effects may be automatically tracked. For example, sweating or hand shaking by the user may be determined when using the system, these situations possibly noting side effect issues. Shaking may be determined by checking a blur of the injection apparatus, checking a blur of the one or more selection parameters, movement of one or more features between frames or the like. Any such blurred numbers or other indicators may be detected by either de-blurring, or using machine learning to teach the system to recognize the blurred number or other indicator.

In a particular embodiment of the invention, an injection apparatus, such as an insulin pen, may be provided with only a predetermined set of numbers in the window indicative of titration level. Thus, the system may read a single number in the middle of the window, or two numbers, one at the top of the window and one at the bottom, thus indicating a titration value therebetween. A poor viewing angle may make it difficult to determine when two such number are present in the window, such as if the user displays the apparatus at an angle in which only one of the two numbers is visible. By calculating and determining a position angle of the injection apparatus, it can be determined whether the reading is a single or double number reading, and whether therefore the number is the exact titration level, or whether there are two numbers in the window.

In order to confirm that a user is the correct user, one or more of a password, facial recognition, voice recognition, usage pattern recognition and the like may be employed.

Returning back to FIG. 3, recognition in the case of an injectable administration apparatus, as noted above, may also comprise confirming relationship of the injectable administration apparatus and a prescribed body part, proper actuation of the administration apparatus, maintaining the administration apparatus in the location for a predetermined period of time, and perhaps proper post administration action, such as cleaning and storing the apparatus, refrigerating the apparatus, cleaning an injection site and the like. Further, voice recognition may be utilized to allow the user to enter commands, and an audio output may be provided for aiding the user in properly adhering to instructions from the system. Additional audio cues may be recognized, such as upon visual confirmation of administration of an injectable or inhalable medication, audio signatures may be employed in order to determine whether insufficient pressure may have been used, or whether a sufficient or extensive period of time has passed from actuation to inhalation. Proper capture of patient actions is very important as the patient only administers the medication once per capture period.

After capture of each step asked of the user, in order to provide real time feedback to the user, and as described above, video capture analysis for each step may then begin at step 330, such analysis comprising analysis of the newly captured video and/or audio. At step 335 it may be determined whether the action has been properly performed, according for example to the process described with respect to FIG. 13, and whether the captured action has been properly analyzed by the system. Various incentives may be provided to the patient to encourage them to administer their medication properly. Thus, in addition to providing various reminders to a patient as is known in the art, points, monetary or other incentive may be provided to the user for actually having medication administration confirmed. Further proper administration with less errors, etc. may be rewarded more highly, thus giving incentive for the patient to concentrate on administration issues and to attempt to have such administration be as accurate and consistent as possible. Such incentives and medication tracking may be used to determine future courses of treatment or payment. For example, if a patient consistently fails to take medication as required, perhaps a different course of treatment requiring fewer medication administrations may be better for this patient. Alternatively, if a medication requires a consistent administration and is very expensive, failure to comply with administration instructions may be cause for an insurance company, prescribing doctor or the like to not renew such a prescription for the patient, thus saving money in a situation where the money was being wasted because of lack of compliance.

If it is determined that administration of the medication did not take place properly, processing may return to step 325 and the user may be once again prompted to perform the action, including additional or alternative instructions to assist the user, again, as noted in FIG. 13. Of course, if this process involves actual administration of injectable medication, it may not be proper to request re-performance of the action, unless it can be determined that the user did not actually administer the medication. If the action has been properly captured, and is able to be analyzed, and it is determined that the user has properly performed the processing step, processing passes to step 345 where it may be determined whether additional captures of additional processing steps if to be performed. If so, processing returns to step 320. If no further captures are required, processing ends at step 350 where the various captured video sequences are stored. These stored sequences may also be made available for human review and involvement, when it is determined that this would be beneficial.

In accordance with one or more alternative embodiments of the invention, additional features may be provided. For example, one or more mobile device additions may be provided, such as heads up displays, mobile glasses or the like, may be employed to read and determine the indicate selection parameter, rather than using the camera of the mobile device directly. Furthermore, a dashboard or other reporting function may allow for a titration level or other selection parameter to be plotted over time, thus giving a time-based profile of usage. As noted above, blood sugar levels, etc. may be correlated with usage, either by reading this information as another selection parameter (but on the input side, i.e. a number from the meter may be recognized in a manner similar to the recognition of the selection parameter in accordance with one or more of the embodiments of the present invention), through wireless or wired connection, or through manual input. Suggested titration levels, for example, may be adjusted in accordance with this information.

If one or more spikes in usage (based upon a user selecting a higher than normal titration level, or one or more automated suggestions for administration being higher than usual based upon entry, either manually or automatically, of one or more measured values from one or roe other devices, as described above, or other unusual situation occurs, the system may provide one or more further instructions to the user on better ways to manage illness. Similar reports may be provided back to a healthcare provider. The system thus may lean the body's reaction to medication, and may therefore better recommend medication levels based upon various inputs. For example, the system may prompt more medication to be administered if the system is provided with a particular level of glucose reading. The system may further request additional information from user upon the recognition of expected or unexpected behavior (eating exercise sleeping), and preferably utilize this information to further recommend medication levels. Pedometers and GPS monitors may further be coupled and employed to provide further information regarding suggested medication levels and other recommended forms of activity. Side effects may be recognized, reported to a healthcare provider, and the system may provide further information to the user to address these side effects. Additionally, performance of desired activity may prompt rewards or other benefits to be provided to the user to therefore further encourage proper behavior. Usability data, buying preferences (time, credit card, pharmacy, location) may also preferably be provided to a centralized location for further analysis as desired.

In addition to reporting this information, the method and system of the invention, in accordance with a still further embodiment of the invention, data related to mediation injection usage patterns, logging of glucose patterns and history, eating history and habits and the like may be provided. By combining these different data sources, including data collected from the patient, data collected from the doctor or other healthcare provider (such a prescription, changes in prescription based upon an office visit, etc.) the system can better provide suggestions to the user on how to use the injection apparatus, when to perform administration, proper dosages, how to avoid side effects, medication interactions and the like. Thus, the system may provide an overall behavior tracking system for diabetes or other disease so that patients can provide the most accurate data to their doctors, and have the best health assistance while using the medication.

Therefore, in accordance with various embodiments of the invention, because a video image of the patient actually administering an injectable or other medication (or other method of medication administration, including but not limited to inhalers, dialysis, and any other medication administration procedure), and a medication level may be captured and analyzed, actual confirmation of administration and an amount of medication that has been administered may be achieved, rather than simply relying on the patient to state that a particular medication or amount was administered. Such a video image may be captured or stored in any appropriate format given a selected type of activity or gesture recognition that is employed in accordance with a particular embodiment of the invention. Such may include full video, biometric data points, recording of movement of an article, such as a bracelet or the like, affixed to the patient or administrator, use of mapping to provide a stick figure or other body movement tracking technique, or gesture or activity recognition to determine movement or the like. The user may be encouraged to use a particular sequence of movement to be confirmed that they are properly administering the medication according to the protocol, thus reducing the possibility of the potential appropriate movements considered to be "correct." Or, as noted above, capture of customized video sequences may be performed so that the user is more likely to repeat these same actions. Indeed, various instructional videos or other appropriate training may be provided to a user to insure they properly administer the medication.

In one or more alternative embodiments of the invention, it may be possible to blur or otherwise de-identify patient information, such as their face, any prescription information noted on the injectable medication apparatus, or the like. In such a manner, the data may first be processed by the local apparatus, and then de-identified before being transmitted to a remote location for further analysis, storage or the like. Furthermore, reading information from a glucose meter or other apparatus may be performed in a similar manner, and thus the need for wireless or wired coupling with the mobile apparatus may be avoided. In such an embodiment similar prompts and the like may be provided to the user to properly position the glucose meter or other device so that one or more pieces of information may be read therefrom by the device implementing the one or more embodiments of the invention.

This captured adherence information may be provided to a healthcare provider, clinical trial manager or the like through a dashboard allowing for the review of information about an individual patient, entire population of patients, or demographically relevant information. Such information may be provided to easily notify the healthcare provider, clinical trial manager or the like of problem patients, demographic groups, medications or the like. One or more dashboards or other reporting mechanisms may be employed as described in copending U.S. patent application Ser. No. 13/189,518, filed Jul. 24, 2011 to Hanina et al., titled "Method and Apparatus for Monitoring Medication Adherence", the entire contents thereof being incorporated herein by reference. Thus, any adherence or other information obtained in accordance with the present invention may be provided to one or more individuals in accordance with one or more methods or systems as described in the '518 application. Thus, accumulated information may be provided to the sponsor of a trial, healthcare providers, insurance companies and the like. This information may further be employed to predict future behavior, such that is a user fails to properly take their medication a particular number of times, and outreach may be performed before the user completely fails in their medication administration.

Through the use of training as described above, a type of administration language may be generated, allowing for extension to other patients, and also allowing for interpretation of reason for differences from a predefined sequence by a patient. Thus, if a patient performs an action differently over time, this difference may provide insight to a reaction to a medication, changes in the patient's medical condition, or the like. It is further anticipated that analysis of large numbers of patients will allow for a more flexible system that may recognize more of a patient's movements, and thus may improve the ability of the system to function properly.

Therefore, in accordance with an embodiment of the invention, a user may perform a predetermined sequence of actions designed to ensure performance of medication administration. Thus, by way of example only, for an injected medication as noted above, the user may be asked to first show a medication to confirm a medication level or other selection parameter and may then be prompted to position the medication administration apparatus relative to a particular body part in a desired manner. Next the user may be prompted to administer the medication, the action of administration being captured on video and audio, and being interpreted to confirm that the medication has been properly administered. Of course, in accordance with this embodiment of the invention, other action sequences may be employed, and may be mixed with other actions to be performed by a patient or caregiver. Thus, by defining a medication adherence protocol as a single or sequence of gestures that may be recognized by a processing system, the accuracy of confirming that a patient has actually taken a particular medication, and the amount of that medication is improved. Through an interactive learning process, the processing system may also learn patient behaviors to be more accurately determine medication adherence, and to remove some of the potential false positives or false negatives. If a caregiver is involved, it is contemplated that the caregiver be provided with a number of gestures indicative of particular actions to be taken, and use of these gestures prompting the system to confirm that these actions are in fact being taken. Thus, a full audit trail of not only the patient, but also the caregiver may be determine, such as whether they approached the patient at the correct times, or that they washed their hands when approaching.

Further uses of the video capture sequences may also be employed, including video capture of responses to questionnaires about current patient states of discomfort, informed consent, example of questions to be asked, video transmission of such questions and the like. The patient may be able to send a video message, pointing to a particular pain or the like, and may include an audio portion as well. Time stamp markers may also be captured to confirm that the user is taking their medication at appropriate times and a number of times a user has taken a particular medication, to confirm whether there are substantial delays between instruction and administration, or for any other time sequence determination. Furthermore, other behavioral markers, such as, by way of example only, shaking hands indicating a particular ailment, or other movements by a patient that may give a hint as to the physical or mental status thereof. Additionally, if the user is taking medication that is improper, or they have already taken, a warning may be provided to warn the user to stop medication administration immediately.

In accordance with various embodiments of the invention, when considering administration of an injectable medication, analysis of adherence video sequences may be employed to determine a likelihood that a patient has actually administered their medication, and have administered a correct amount of medication. Thus, based upon video and audio cues determined related to positioning and use of the medication administration apparatus, it may be determined that the patient is having problems properly positioning the apparatus, and therefore the system is unsure that the patient has administered the medication properly. Low confidence in proper administration based upon failure to properly position the apparatus, failure to record audio signals indicative of proper administration or the like may be employed to determine whether a patient should be retrained, via the automated training system described herein, by automated contact, or by individual personal contact. This determination of low confidence of administration, even if it is ultimately determined that administration likely took place, may still be utilized to determine whether training or other actions may be taken. Such confidence levels may be used, in accordance with a desired algorithm or the like, to provide an overall picture of medication administration by a patients or group of patients, thus allowing for intervention, encouragement, training or the like to be provided when it appears that actions are changing, but not necessarily waiting until a critical issue is discovered.

The method may be implemented on a general purpose computer, a purposefully built system, or any other computing system including one or more non-transitory computer readable storage medium. Various communication systems may be employed, such as wifi, cellular or other private network. The computing system may be a local device including processor, memory, camera and display. Alternatively, one or more of these elements may be located at a remote location, such as employing cloud storage and/or processing. It is further contemplated that the method and apparatus of the invention allow for integration with one or more audio or video conferencing systems, thus receiving and/or providing information there through. Thus, a user may employ a standard video conferencing tool or system, and have this information be coupled to a mobile or other device being used in accordance with an embodiment of the present invention.

Therefore, in accordance with the invention, a method and apparatus are provided that allow for the automated confirmation of adherence to administration protocol for medication, and provide for a most sophisticated method for confirming and studying methods of administration of such prescription medication.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description and the following claims are intended to cover all of the generic and specific features of the invention herein described and all statements of the scope of the invention which, as a matter of language, might be said to fall there between.

What is claimed:

1. A non-transitory computer readable storage medium having a computer program stored thereon, the computer program, when executed by a computing device, causing the computing device to perform operations comprising:

providing a first set of instructions on a display of the computing device instructing placement of a medical measurement device for measurement of a measured medical value directly from a user, wherein the first set of instructions comprises instructions to place, within a field of view of an image capture device, a numerical indicator of the medical measurement device indicative of the measured medical value;

imaging, by the image capture device of the computing device, the numerical indicator indicative of the measured medical value of the medical measurement device;

comparing, through recognition of the numerical indicator indicative of the measured medical value, the measured medical value to a predetermined amount;

providing a second set of instructions on the display of the computing device to the user subsequent to comparing the measured medical value and the predetermined amount; and confirming that a post-measurement operation of a second medical device satisfies one or more criteria in response to the user following the provided second set of instructions, wherein the first set of instructions on the display of the computing device comprises an image representative of the medical measurement device displayed alongside one or more geometric elements, and wherein the image representative of the medical measurement device, the one or more geometric elements, or both, are adjusted visually in real time, as the user moves the medical measurement device, to reflect an actual position of the medical measurement device relative to a target position of the medical measurement device, in order to aid the user in positioning the medical measurement device.

2. The non-transitory computer readable storage medium of claim 1, wherein the second medical device comprises an injectable medication apparatus.

3. The non-transitory computer readable storage medium of claim 2, wherein the post-measurement operation of the injectable medication apparatus comprises injection of a medication employing a retractable needle.

4. The non-transitory computer readable storage medium of claim 2, wherein the operations comprise providing, on the display, a numerical indication of a titration level of medication to be injected by the injectable medication apparatus.

5. The non-transitory computer readable storage medium of claim 2, wherein the injectable medication apparatus comprises an insulin injection pen.

6. The non-transitory computer readable storage medium of claim 1, wherein the operations further comprise providing one or more audio instructions accompanying the first set of instructions on the display of the computing device.

7. A non-transitory computer readable storage medium having a computer program stored thereon, the computer program, when executed by a computing device, causing the computing device to perform operations comprising:
  providing a first set of instructions on a display of the computing device, wherein the first set of instructions comprises instructions to place, within a field of view of an image capture device of the computing device, a medical measurement device, including placement within the field of view of one or more displayed characters indicative of a measured medical value output from the medical measurement device, wherein the first set of instructions comprises instructions to orient the medical measurement device with respect to the image capture device,
  wherein the first set of instructions on the display of the computing device comprises an image representative of the medical measurement device displayed alongside one or more geometric elements, and wherein the image representative of the medical measurement device, the one or more geometric elements, or both, are adjusted visually in real time, as a user moves the medical measurement device, to reflect an actual position of the medical measurement device relative to a target position of the medical measurement device, in order to aid the user in positioning the medical measurement device;
  imaging, by the image capture device, one or more images of the one or more displayed characters indicative of the measured medical value output from the medical measurement device;
  determining, based on the one or more images, the measured medical value output from the medical measurement device;
  comparing the measured medical value output from the medical measurement device to a predetermined value; and
  subsequent to comparing the measured medical value to the predetermined value, providing on the display of the computing device a second set of instructions for adjusting a value of a second medical device.

8. The non-transitory computer readable storage medium of claim 7, wherein the operations comprise changing the predetermined value in accordance with a prescription.

9. The non-transitory computer readable storage medium of claim 7, wherein the operations comprise changing the predetermined value in accordance with additional information provided by a user.

10. The non-transitory computer readable storage medium of claim 7, wherein the operations comprise:
  providing an additional set of instructions on the display of the computing device, the additional set of instructions comprising instructions to place the second medical device within the field of view of the image capture device including placement of one or more characters displayed by the second medical device and indicating a measured value output from the second medical device; and
  imaging, by the image capture device of the computing device, one or more images of the one or more characters displayed by the second medical device; and
  determining, based on the one or more images of the one or more characters displayed by the second medical device, the measured value output from the second medical device.

11. The non-transitory computer readable storage medium of claim 7, wherein the operations comprise confirming that a post-measurement operation of the second medical device satisfies one or more criteria.

12. The non-transitory computer readable storage medium of claim 11 wherein the post-measurement operation of the second medical device comprises retraction of a needle associated therewith.

13. The non-transitory computer readable storage medium of claim 11, wherein the post-measurement operation of the second medical device comprises return of an indication of a titration level to zero.

14. A system for reading a value from a medical measurement device, the system comprising:
  a display of a computing device;
  an image capture device; and
  a processor configured
    to output to the display a first set of instructions, wherein the first set of instructions comprises instructions to place, within a field of view of the image capture device, a medical measurement device for measurement of a medical value directly from a user, and to place, within the field of view, one or more characters displayed by the medical measurement device and indicative of the medical value,
    wherein the first set of instructions on the display of the computing device comprises an image representative of the medical measurement device displayed alongside one or more geometric elements, and wherein the image representative of the medical measurement device, the one or more geometric elements, or both, are adjusted visually in real time, as the user moves the medical measurement device, to reflect an actual position of the medical measurement device relative to a target position of the medical measurement device, in order to aid the user in positioning the medical measurement device
    to receive from the image capture device one or more images of the one or more characters, and
    to determine the medical value based on the received one or more images of the one or more characters, and to output to the display a second set of instructions, the second set of instructions comprising instructions to change one or more values on a second medical device based on the medical value.

15. The system of claim 14, wherein the processor is a first processor, and further comprising:
   a transmission system operable to transmit one or more recorded data comprising the medical value and a time of imaging of the one or more images of the one or more characters; and
   a second processor located at a processing location remote from the first processor, the display and the image capture device, wherein the second processor is operable to receive the recorded data via the transmission system, process the recorded data, and provide the processed recorded data to a second user.

16. The non-transitory computer readable storage medium of claim 1, wherein the one or more geometric elements comprise multiple concentric circles, and wherein a center circle of the multiple concentric circles represents the target position of the medical measurement device.

17. The non-transitory computer readable storage medium of claim 1, wherein at least one of the one or more geometric elements changes color when the medical measurement device is positioned at the target position.

18. The non-transitory computer readable storage medium of claim 1, wherein the one or more geometric elements comprise a set of guidance tracks on which successive positions for the medical measurement device are superimposed.

* * * * *